United States Patent
Kang et al.

(10) Patent No.: US 12,191,029 B2
(45) Date of Patent: Jan. 7, 2025

(54) ELECTRONIC DEVICE AND METHOD FOR RECOGNIZING CONTEXT THEREOF

(71) Applicant: Samsung Electronics Co., Ltd., Gyeonggi-do (KR)

(72) Inventors: Kihoon Kang, Gyeonggi-do (KR); Taekeun Kim, Gyeonggi-do (KR); Kihong Min, Gyeonggi-do (KR); Sunghun Shin, Gyeonggi-do (KR); Kihun Eom, Gyeonggi-do (KR); Kyeongmun Jo, Gyeonggi-do (KR)

(73) Assignee: Samsung Electronics Co., Ltd (KR)

( * ) Notice: Subject to any disclaimer, the term of this patent is extended or adjusted under 35 U.S.C. 154(b) by 842 days.

(21) Appl. No.: 17/178,738

(22) Filed: Feb. 18, 2021

(65) Prior Publication Data
US 2021/0257086 A1    Aug. 19, 2021

(30) Foreign Application Priority Data
Feb. 19, 2020  (KR) .................. 10-2020-0020712

(51) Int. Cl.
*A61B 5/00* (2006.01)
*A61B 5/25* (2021.01)
(Continued)

(52) U.S. Cl.
CPC ............... *G16H 40/60* (2018.01); *A61B 5/25* (2021.01); *G01L 19/0092* (2013.01);
(Continued)

(58) Field of Classification Search
CPC .......... G16H 40/60; G16H 40/63; A61B 5/25; A61B 5/0048; A61B 5/0053;
(Continued)

(56) References Cited

U.S. PATENT DOCUMENTS

| 6,580,943 B2 * | 6/2003 | Nissila | A61B 5/0006 600/509 |
| 10,154,460 B1 * | 12/2018 | Miller | A61B 5/7278 |

(Continued)

FOREIGN PATENT DOCUMENTS

| JP | 2017-093630 | 6/2017 |
| KR | 1020090009831 | 1/2009 |

(Continued)

OTHER PUBLICATIONS

International Search Report dated Jun. 9, 2021 issued in counterpart application No. PCT/KR2021/002096, 7 pages.

*Primary Examiner* — Eun Hwa Kim
*Assistant Examiner* — Ana Veruska Guerrero
(74) *Attorney, Agent, or Firm* — The Farrell Law Firm, P.C.

(57) ABSTRACT

A method is provided. The method includes identifying whether an amount of change in the pressure detected through an atmospheric pressure sensor is greater than or equal to a specified first threshold, in response to the amount of change in the pressure being greater than or equal to the first threshold, waking up a biometric sensor module including a plurality of electrodes in which some of the plurality of electrodes are disposed to come into contact with a body part of a user when the electronic device is worn, and others thereof are disposed to not come into contact with a body part of the user when the electronic device is worn, and identifying whether an interrupt signal, indicating that a state in which the plurality of electrodes are electrically connected is maintained for a specified first time or more, is received from the biometric sensor module.

20 Claims, 23 Drawing Sheets

(51) Int. Cl.
*G01L 19/00* (2006.01)
*G06F 3/01* (2006.01)
*G16H 40/60* (2018.01)
*A61B 5/02* (2006.01)
*A61B 5/024* (2006.01)
*A61B 5/15* (2006.01)
*A61B 5/282* (2021.01)

(52) U.S. Cl.
CPC ............ *G06F 3/011* (2013.01); *A61B 5/0048* (2013.01); *A61B 5/0053* (2013.01); *A61B 5/0077* (2013.01); *A61B 5/02* (2013.01); *A61B 5/024* (2013.01); *A61B 5/02427* (2013.01); *A61B 5/02438* (2013.01); *A61B 5/150824* (2013.01); *A61B 5/282* (2021.01); *A61B 5/68* (2013.01); *A61B 5/6801* (2013.01); *A61B 5/6802* (2013.01); *A61B 5/681* (2013.01); *A61B 5/6813* (2013.01); *A61B 5/6824* (2013.01); *A61B 5/683* (2013.01); *A61B 5/6831* (2013.01); *A61B 2560/0209* (2013.01); *A61B 2560/0257* (2013.01); *A61B 2560/0462* (2013.01); *A61B 2560/0468* (2013.01); *A61B 2562/02* (2013.01); *A61B 2562/0209* (2013.01); *A61B 2562/0247* (2013.01); *A61B 2562/029* (2013.01); *A61B 2562/04* (2013.01); *G01L 2019/0053* (2013.01)

(58) Field of Classification Search
CPC ......... A61B 5/0077; A61B 5/02; A61B 5/024; A61B 5/02427; A61B 5/02438; A61B 5/150824; A61B 5/282; A61B 5/68; A61B 5/6801; A61B 5/6802; A61B 5/681; A61B 5/6813; A61B 5/6824; A61B 5/683; A61B 5/6831; A61B 2560/0209; A61B 2560/0257; A61B 2560/0462; A61B 2560/0468; A61B 2562/02; A61B 2562/0209; A61B 2562/0247; A61B 2562/029; A61B 2562/04; A61B 5/0245; A61B 5/332; A61B 2560/0242; A61B 2560/0266; A61B 2560/029; A61B 5/02416; A61B 5/6843; A61B 5/72; G01L 19/0092; G01L 2019/0053; G06F 3/011; G06F 3/016

See application file for complete search history.

(56) References Cited

U.S. PATENT DOCUMENTS

| | | | |
|---|---|---|---|
| 10,227,117 B2 * | 3/2019 | Easterling | B63G 8/001 |
| 2009/0185451 A1 | 7/2009 | Rochat | |
| 2014/0278220 A1 * | 9/2014 | Yuen | A61B 5/681 |
| | | | 702/150 |
| 2016/0206241 A1 * | 7/2016 | Cho | A61B 5/14521 |
| 2017/0086743 A1 | 3/2017 | Bushnell et al. | |
| 2017/0094177 A1 * | 3/2017 | Hayashi | G06F 16/51 |
| 2017/0134022 A1 * | 5/2017 | Kim | H03K 17/955 |
| 2017/0185856 A1 * | 6/2017 | Park | G06V 40/70 |
| 2017/0193314 A1 * | 7/2017 | Kim | G06F 3/147 |
| 2018/0235542 A1 * | 8/2018 | Yun | A61B 5/6843 |
| 2019/0076063 A1 * | 3/2019 | Kent | A61B 5/1118 |

FOREIGN PATENT DOCUMENTS

| | | | |
|---|---|---|---|
| KR | 20170006537 A | * | 7/2015 |
| KR | 1020170006537 | | 1/2017 |
| KR | 10-2073213 | | 2/2020 |

* cited by examiner

ELECTRONIC DEVICE AND METHOD FOR RECOGNIZING CONTEXT THEREOF

CROSS-REFERENCE TO RELATED APPLICATION(S)

This application is based on and claims priority under 35 U.S.C. § 119 to Korean Patent Application No. 10-2020-0020712, filed on Feb. 19, 2020, in the Korean Intellectual Property Office, the disclosure of which is incorporated by reference herein in its entirety.

BACKGROUND

1. Field

The present disclosure relates generally to an electronic device and a method for recognizing (or perceiving) contexts thereof.

2. Description of Related Art

Electronic devices (e.g., mobile terminals, smart phones, or wearable terminals) may provide various functions (e.g., a music playback function, a navigation function, a short-range wireless communication function (e.g., Bluetooth™, Wi-Fi, or near field communication (NFC)), a fingerprint recognition function, or an electronic payment function).

Recently, electronic devices have a waterproof function applied thereto (or strengthened therein). For example, as the waterproof function is applied (or strengthened), a user may perform various underwater activities (e.g., swimming, scuba diving, and snorkeling) while wearing a wearable electronic device.

Recent electronic devices include various biometric sensors (e.g., a photoplethysmogram sensor or an electrocardiogram sensor) to provide health-related services. For example, recent electronic devices may measure biometric information (e.g., a heart rate, an electrocardiogram, body fat/body composition, or blood pressure) of the user using various biometric sensors, and may provide various health-related services using the measured biometric information.

An electronic device may execute a function (or a mode) suitable for an external context. For example, the electronic device may recognize an external context through user input, and may execute a function suitable for the external context. However, in the case of recognizing the external context according to user input, there may be an inconvenience in which the user must provide an input for executing an appropriate function every time according to the external context.

Alternatively, the electronic device may recognize an external context through one or more sensors, and may automatically execute a function appropriate to the recognized external context. For example, the electronic device may measure a change in atmospheric pressure through an atmospheric pressure sensor, may recognize that the electronic device is underwater if the change in atmospheric pressure is greater than or equal to a specified threshold, and may automatically execute an underwater mode. However, in the case of recognizing an external context using a single sensor, the electronic device may not accurately recognize the external context, and in the case of using multiple sensors, the unit cost of the electronic device may increase, and current consumption may increase.

SUMMARY

The present disclosure has been made to address at least the disadvantages described above and to provide at least the advantages described below.

In accordance with an aspect of the present disclosure, an electronic device is provided. The electronic device includes an atmospheric pressure sensor configured to measure pressure, a biometric sensor module configured to measure biometric information on a user, a processor operatively connected to the atmospheric pressure sensor and the biometric sensor module, and a memory operatively connected to the processor. The biometric sensor module includes a plurality of electrodes, some of the plurality of electrodes are disposed to come into contact with a body part of the user when the electronic device is worn, and others of the plurality of electrodes are disposed to not come into contact with a body part of the user when the electronic device is worn, and the biometric sensor module is configured to identify whether a change from a first state, in which the some of the plurality of electrodes are electrically connected, into a second state, in which all of the plurality of electrodes are electrically connected, is detected, identify whether the second state is maintained for a specified first time or more in response to the change into the second state being detected, and transmit an interrupt signal to the processor in response to the second state being maintained for the specified first time or more. The memory stores instructions that when executed, cause the processor to identify an amount of change in the pressure detected through the atmospheric pressure sensor in response to reception of the interrupt signal and determine that the electronic device is in a specified first context in response to the amount of change in the pressure being greater than or equal to a specified first threshold.

In accordance with an aspect of the present disclosure, an electronic device is provided. The electronic device includes an atmospheric pressure sensor configured to measure pressure, a biometric sensor module configured to measure biometric information on a user, a processor operatively connected to the atmospheric pressure sensor and the biometric sensor module, and a memory operatively connected to the processor. The biometric sensor module includes a plurality of electrodes and some of the plurality of electrodes are disposed to come into contact with a body part of the user when the electronic device is worn, and others of the plurality of electrodes are disposed to not come into contact with a body part of the user when the electronic device is worn. The biometric sensor module is configured to be activated in response to a wake-up signal being received from the processor, identify whether a state in which the plurality of electrodes are electrically connected is maintained for a specified first time or more, and transmit an interrupt signal to the processor in response to the state being maintained for the specified first time or more. The memory stores instructions that, when executed, cause the processor to transmit the wake-up signal to the biometric sensor module in response to an amount of change in the pressure measured through the atmospheric pressure sensor being greater than or equal to a specified first threshold, and determine that the electronic device is in a specified first context in response to reception of the interrupt signal from the biometric sensor module.

In accordance with an aspect of the present disclosure, a method for recognizing a context of an electronic device is provided. The method includes identifying whether an amount of change in the pressure detected through an atmospheric pressure sensor is greater than or equal to a specified first threshold, in response to the amount of change in the pressure being greater than or equal to the first threshold, waking up a biometric sensor module including a plurality of electrodes in which some of the plurality of electrodes are disposed to come into contact with a body part of a user when the electronic device is worn, and others thereof are disposed to not come into contact with a body part of the user when the electronic device is worn, identifying whether an interrupt signal, indicating that a state in which the plurality of electrodes are electrically connected is maintained for a specified first time or more, is received from the biometric sensor module, and determining that the electronic device is in a specified first context in response to reception of the interrupt signal.

BRIEF DESCRIPTION OF THE DRAWINGS

The above and other aspects, features and advantages of certain embodiments of the disclosure will be more apparent from the following detailed description taken in conjunction with the accompanying drawings, in which.

DETAILED DESCRIPTION

Hereinafter, a description of various example embodiments will be provided with reference to attached drawings. Various embodiments are illustrated in drawings and the relevant detailed description is disclosed, but these example embodiments are not intended to limit various embodiments to a specific form. For example, embodiments can be variously changed, and it would be apparent to a person of ordinary skill in the art.

Figure 1:
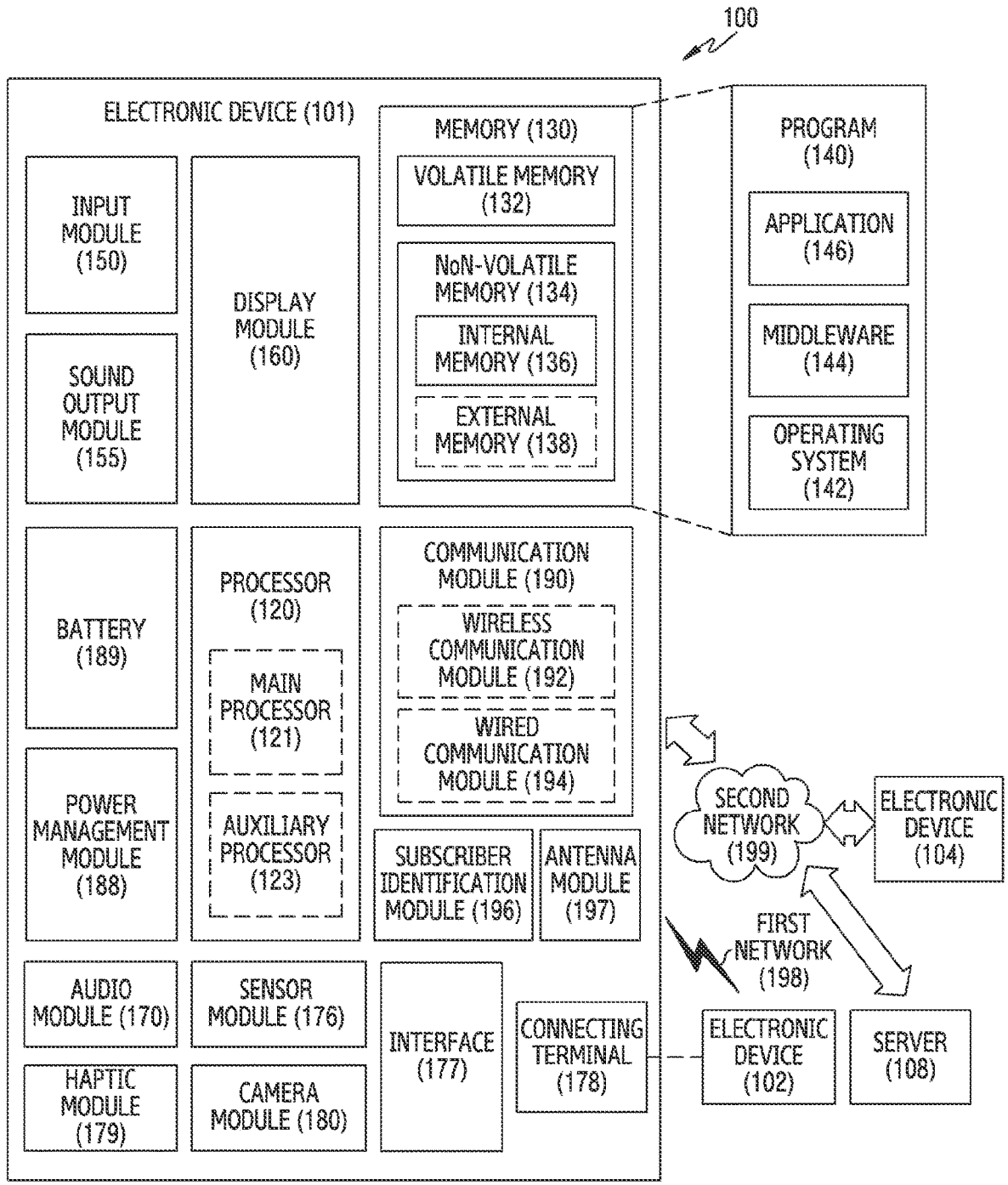
FIG. 1 is a block diagram of an electronic device in a network environment, according to an embodiment.

FIG. 1 is a block diagram illustrating an electronic device 101 in a network environment 100 according to an embodiment.

Referring to FIG. 1, the electronic device 101 in the network environment 100 may communicate with an electronic device 102 via a first network 198 (e.g., a short-range wireless communication network), or at least one of an electronic device 104 or a server 108 via a second network 199 (e.g., a long-range wireless communication network). The electronic device 101 may communicate with the electronic device 104 via the server 108. The electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. As at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. The processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). The auxiliary processor 123 (e.g., an ISP or a CP) may be implemented as part of another component (e.g., the camera module 180 or the communication module 190) functionally related to the auxiliary processor 123. The auxiliary processor 123 (e.g., the NPU) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers.

The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network, or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. The receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. The audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. The sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. The interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). The connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. The haptic module 179 may include, for example, a motor, a piezoelectric element, or an electric stimulator.

The camera module 180 may capture a still image or moving images. The camera module 180 may include one or more lenses, image sensors, ISPs, or flashes.

The power management module 188 may manage power supplied to the electronic device 101. The power management module 188 may be implemented as at least part of, for example, a power management integrated circuit (PMIC).

The battery 189 may supply power to at least one component of the electronic device 101. The battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more CPs that are operable independently from the processor 120 (e.g., the AP) and supports a direct (e.g., wired) communication or a wireless communication. The communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). The wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. The antenna module 197 may include an antenna including a radiating element including a conductive material or a conductive pattern formed in or on a substrate (e.g., a printed circuit board (PCB)). The antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. Another component (e.g., a radio frequency integrated circuit (RFIC)) other than the radiating element may be additionally formed as part of the antenna module 197.

The antenna module 197 may form an mmWave antenna module. The mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. All or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. The external electronic device 104 or the server 108 may be included in the second network 199. The electronic device 101 may be applied to intelligent services (e.g., smart home, smart city, smart car, or healthcare) based on 5G communication technology or IoT-related technology.

The electronic device may utilize (or share) a sensor for a first purpose as a sensor for a second purpose. A biometric sensor for measuring information related to the health of a user (a first purpose) may be used as a sensor for recognizing contexts of the electronic device (a second purpose). In addition, if the electronic device includes a separate sensor for the second purpose, the sensor for the first purpose and the sensor for the second purpose may be combined to improve the accuracy of recognizing contexts.

The contexts may include underwater (shallow dive or deep dive), swimming, out of water, and/or loss. For the convenience of explanation, hereinafter, various embodiments of the disclosure will be described based on an example of recognizing the various contexts (e.g., underwater, swimming, out of water, and/or loss) using a biometric sensor and an atmospheric pressure sensor.

Figure 2A:
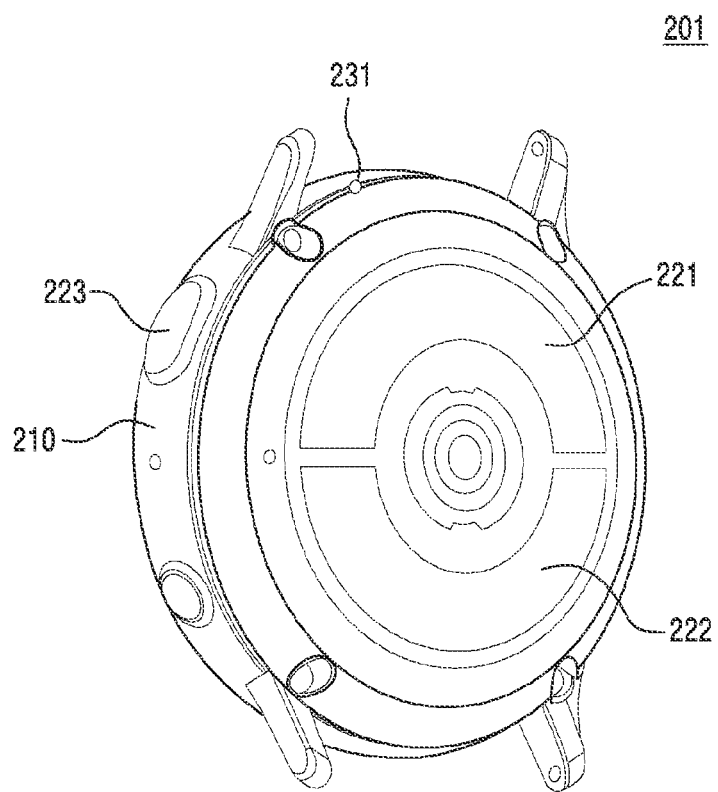
FIG. 2A is a diagram illustrating an electronic device, according to an embodiment.
Figure 2B:
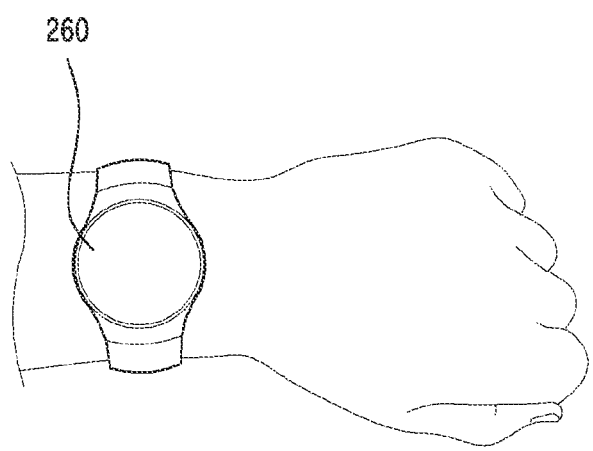
FIG. 2B is a diagram illustrating an example of wearing an electronic device, according to an embodiment.

FIG. 2A is a diagram illustrating an electronic device, according to an embodiment. FIG. 2B is a diagram illustrating an example of wearing an electronic device, according to an embodiment.

Referring to FIG. 2A and FIG. 2B, an electronic device 201 (e.g., the electronic device 101) may be a wearable electronic device in the form of a watch. The electronic device 201 may be a smart watch.

The electronic device 201 may have a plurality of electrodes 221, 222, and 223 and a vent hole 231, which are disposed (or formed) in a housing 210.

The plurality of electrodes 221, 222, and 223 may come into contact with a body part of a user so that a biometric sensor module is able to acquire biometric information. A first electrode 221 and a second electrode 222, among the plurality of electrodes 221, 222, and 223, may be disposed on the rear surface of the electronic device 201 so as to come into contact with a body part (e.g., a wrist) of the user when the electronic device 201 is worn as shown in FIG. 2B. The first electrode 221 and the second electrode 222 may be disposed to be spaced a predetermined distance apart from each other.

The third electrode 223 may be disposed on the side surface of the electronic device 201 so as not to come into contact with a body part of the user when the electronic device 201 is worn as shown in FIG. 2B. The third electrode 223, as shown in FIG. 2A, may be configured in the form of a button disposed on the side surface of the electronic device 201. The third electrode 223 may be configured as a stem of the electronic device 201 or as a part of the housing 210. The third electrode 223 may be disposed on the front surface of the electronic device 201. The third electrode 223 may be disposed or included in the display 260 in the form of a transparent electrode (e.g., indium tin oxide (ITO)). A plurality of third electrodes 223 may be provided. The plurality of third electrodes 223 may operate in a single channel or in different channels from each other.

The vent hole 231 may be provided on the side surface of the housing 210 to allow the air or the water to enter and exit an atmospheric pressure sensor. The vent hole 231 may allow the air to enter and exit the position in which the atmospheric pressure sensor is disposed if the electronic device 201 is located in the atmosphere, and may allow the water to enter and exit the position in which the atmospheric pressure sensor is positioned if the electronic device 201 is located underwater. In general, the atmospheric pressure sensor that measures (or detects) the pressure of air (atmospheric pressure) may measure the pressure of water (water pressure) within a predetermined range (e.g., in water 1 meter deep) when the atmospheric pressure sensor is located underwater.

Figure 3:
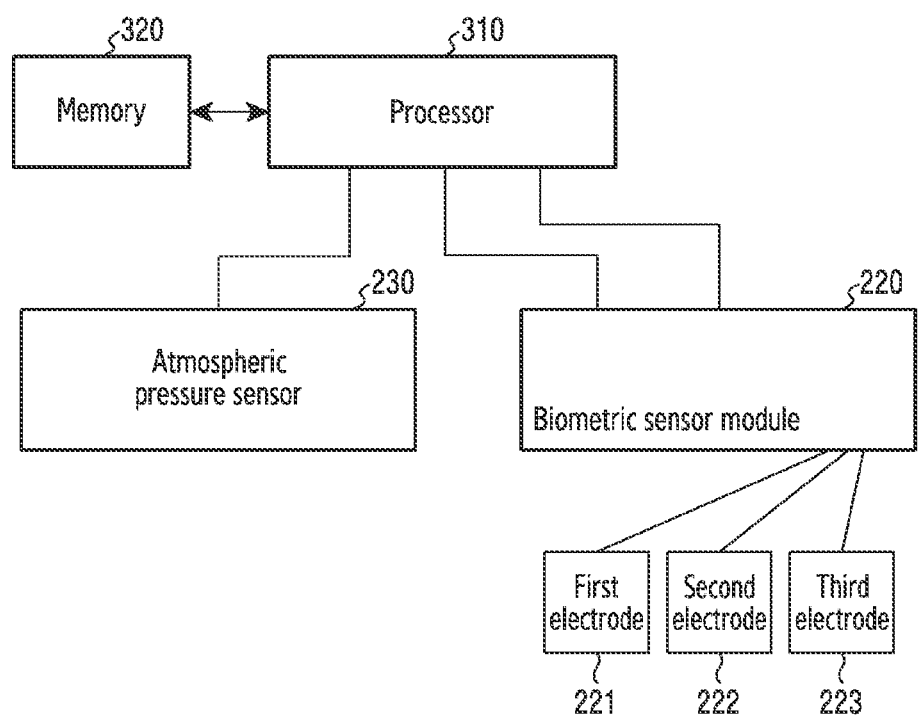
FIG. 3 is a block diagram showing the configuration of an electronic device, according to an embodiment.
Figure 4A:
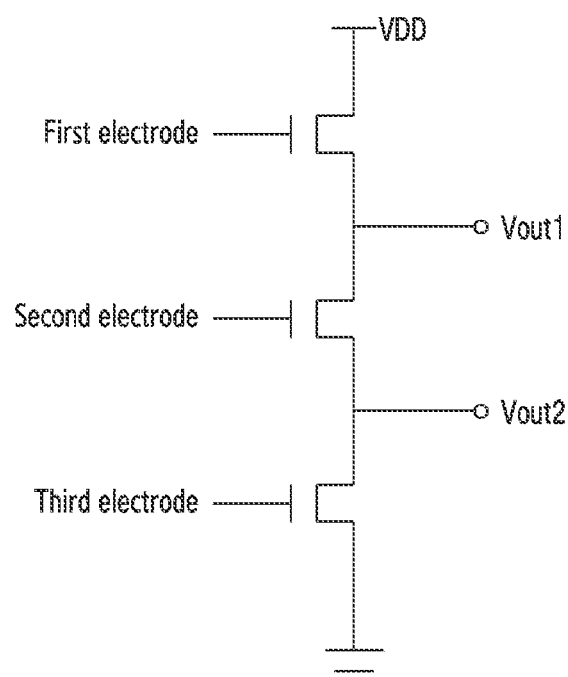
FIG. 4A is a diagram illustrating a method of detecting an electrode state of a biometric sensor module, according to an embodiment.
Figure 4B:
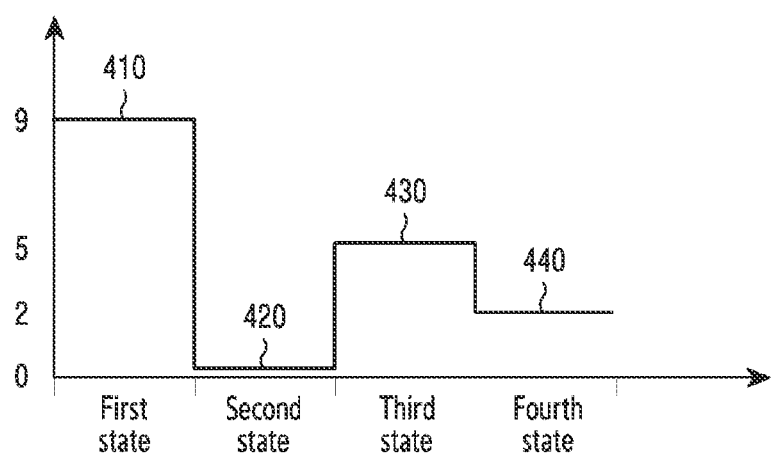
FIG. 4B is a diagram illustrating a change in the state of a biometric sensor module, according to an embodiment.

FIG. 3 is a block diagram showing the configuration of an electronic device, according to an embodiment. FIG. 4A is a diagram illustrating a method of detecting an electrode state of a biometric sensor module, according to an embodiment. FIG. 4B is a diagram illustrating a change in the state of a biometric sensor module, according to an embodiment.

Figure 5:
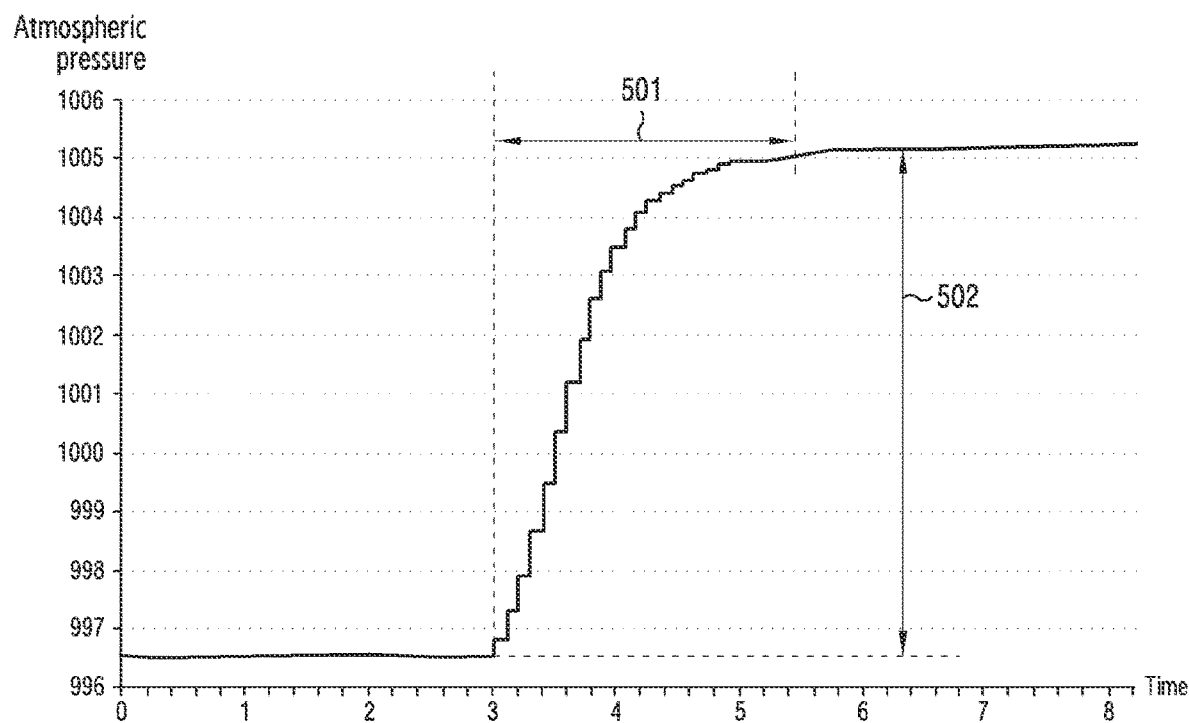
FIG. 5 is a graph showing a change in an atmospheric pressure sensor, according to an embodiment.

FIG. 5 is a graph showing a change in an atmospheric pressure sensor, according to an embodiment.

Referring to FIGS. 3 to 5, an electronic device 201 (e.g., the electronic device 101) may include a processor 310 (e.g., the processor 120), a biometric sensor module 220, an atmospheric pressure sensor 230, and a memory 320 (e.g., the memory 130).

The processor 310 may control a function of recognizing contexts of the electronic device 201. The processor 310 may recognize various external contexts (e.g., underwater, swimming, out of water, and/or loss), based on the connection states of the first electrode 221 to the third electrode 223, which are detected through the biometric sensor module 220, and/or a change in the pressure (atmospheric pressure or water pressure) detected through the atmospheric pressure sensor 230. The processor 310 may execute a function (or may operate in a specified mode) suitable for (or matched with) the recognized context. This will be described in detail later with reference to FIGS. 7 to 17.

The memory 320 may store instructions that, when executed, cause the processor 310 to recognize various contexts of the electronic device 201 using the biometric sensor module 220 and/or the atmospheric pressure sensor 230. The memory 320 may match various contexts with specific functions (or modes), and may store the same therein.

The biometric sensor module 220 may measure health information (e.g., biometric information) of the user. The biometric sensor module 220 may include a galvanic skin response (GSR) sensor, an electrocardiogram (ECG) sensor, and a body-fat measurement sensor. The biometric sensor module 220 may include the first electrode 221, the second electrode 222, and the third electrode 223.

The first electrode 221 may come into contact with a body part of the user when the electronic device 201 is worn. If a function of measuring the biometric information is executed, the first electrode 221 may allow current to flow from the biometric sensor module 220 to the body of the user, or may detect the current flowing through the body of the user.

The second electrode 222 may come into contact with a body part of the user when the electronic device 201 is worn. The second electrode 222 may play the role of the ground. If a function of measuring the biometric information is executed, the second electrode 222, as shown in FIG. 4A, may play the role of a reference (e.g., act as a common ground) for the signal measurement through the first electrode 221 and the third electrode 223.

When the electronic device 201 is worn, the third electrode 223 may not come into contact with a body part (e.g., a wrist of a left hand) with which the first electrode 221 and the second electrode 222 are in contact, and may be exposed to the outside. The user may touch (come into contact with) the third electrode 223 using other body parts (e.g., a right arm, a right hand, or fingers of the right hand) in order to measure the biometric information. If other body parts of the user come into contact with the third electrode 223, the third electrode 223 may allow current to flow from the biometric sensor module 220 to the other body parts, or may detect the current flowing through the other body parts of the user.

The biometric sensor module 220 may detect an electrical connection state of the first electrode 221, the second electrode 222, and the third electrode 223. The biometric sensor module 220 may detect the electrical connection state of the first electrode 221, the second electrode 222, and the third electrode 223, based on a combination of a first output Vout1 between the first electrode 221 and the second electrode 222, and a second output Vout2 between the second electrode 222 and the third electrode 223, as shown in FIG. 4A. As shown in Table 1 below, the biometric sensor module 220 may determine that the electronic device is in a first state in which the first electrode 221 and the second electrode 222 are electrically connected if the first output Vout1 is greater than or equal to a specified value and if the second output Vout2 is less than a specified value, may determine that the electronic device is in a second state in which the first electrode 221, the second electrode 222, and the third electrode 223 are electrically connected if the first output Vout1 is greater than or equal to the specified value and if the second output Vout2 is greater than or equal to the specified value, may determine that the electronic device is in a third state in which the first electrode 221, the second electrode 222, and the third electrode 223 are not electrically connected if the first output Vout1 is less than the specified value and if the second output Vout2 is less than the specified value, and may determine that the electronic device is in a fourth state in which the second electrode 222 and the third electrode 223 are electrically connected if the first output Vout1 is less than the specified value and if the second output Vout2 is greater than or equal to the specified value.

TABLE 1

| | First output (Vout 1) | Second output (Vout 2) |
|---|---|---|
| First electrode and second electrode are connected (first state) | 1 (High) | 0 (Low) |
| First electrode, second electrode, and third electrode are connected (second state) | 1 (High) | 1 (High) |
| No electrode is connected (third state) | 0 (Low) | 0 (Low) |
| Second electrode and third electrode are connected (fourth state) | 0 (Low) | 1 (High) |

The biometric sensor module 220 may store detected state information in a specified register (e.g., a flag). The biometric sensor module 220, as shown in FIG. 4B, may store a first value (e.g., "9") in the register if the first state 410 is determined, may store a second value (e.g., "0") in the register if the second state 420 is determined, may store a third value (e.g., "5") in the register if the third state 430 is determined, and may store a fourth value (e.g., "2") in the register if the fourth state 440 is determined.

The biometric sensor module 220 may transmit an interrupt signal to the processor 310 if a state change corresponding to wearing of the electronic device 201 and/or entering the water is detected. If the first electrode 221 and the second electrode 222 are electrically connected, the biometric sensor module 220 may transmit an interrupt signal to the processor 310. In this case, the processor 310 may determine that the electronic device 201 is worn on the body of the user, based on the state information stored in the register. The biometric sensor module 220 may transmit an interrupt signal to the processor 310 if the first electrode 221, the second electrode 222, and the third electrode 223 are electrically connected. In this case, the processor 310 may determine that the electronic device 201 is underwater based on the state information stored in the register. This is due to the fact that when the electronic device 201 stays underwater, the first electrode 221, the second electrode 222, and the third electrode 223 are electrically connected by means of the conductive property of water. The biometric sensor module 220 may transmit an interrupt signal to the processor 310 if the first electrode 221, the second electrode 222, and the third electrode 223 are electrically connected in the state in which the function of measuring the biometric information is not executed.

The biometric sensor module 220 may transmit an interrupt signal to the processor 310 if the state in which the first electrode 221, the second electrode 222, and the third electrode 223 are electrically connected is maintained for a specified first time or more. This is intended to prevent the electronic device 201 from malfunctioning as if the electronic device 201 were underwater when the first electrode 221, the second electrode 222, and the third electrode 223 are electrically connected due to unintentional and momentary contact between the user's body (e.g., a hand) and the third electrode 223. If a change from the second state into the first state is detected, the biometric sensor module 220 may notify the processor 310 of the state change. The state change may be notified by an interrupt method.

The biometric sensor module 220 may be activated if the amount of change in the pressure detected through the atmospheric pressure sensor 230 is greater than or equal to a first threshold. This is due to the fact that current consumption may be relatively high if the biometric sensor module 220 is continuously maintained in the active state in order to determine whether or not the electronic device enters the water.

The atmospheric pressure sensor 230 may measure the pressure of the air (atmospheric pressure) or the underwater pressure (water pressure) within a predetermined range (e.g., in water 1 meter deep). The atmospheric pressure sensor 230 may measure the pressure of the air or water introduced through a vent hole (e.g., the vent hole 231 in FIG. 2A). The atmospheric pressure sensor 230 may remain in the active state (e.g., always-on) if a context recognition function of the electronic device 201 is turned on (or executed). The atmospheric pressure sensor 230 may continuously or periodically measure the pressure. The atmospheric pressure sensor 230 may transmit the measured pressure to the processor 310. Alternatively, the atmospheric pressure sensor 230 may store the measured pressure in a specified area of the memory 320 for a predetermined time.

The atmospheric pressure sensor 230 may be used to detect whether or not the electronic device 201 enters the water. The pressure detected through the atmospheric pressure sensor 230, as shown in FIG. 5, may increase by a specific amount 502 (about 8.5 hectopascal (hPa)) within a specific time 501 (about 3 seconds) when the electronic device enters the water from the atmosphere. Based on these characteristics, if the pressure detected through the atmospheric pressure sensor 230 changes (e.g., increases) by a first threshold (e.g., 8 hPa) or more, the processor 310 may determine that the electronic device is underwater. On the other hand, if the pressure detected through the atmospheric pressure sensor 230 changes (e.g., decreases) by the first threshold (e.g., 8 hPa) or more in the state in which the electronic device is determined to stay underwater, the processor 310 may determine that the electronic device has come out of the water.

The atmospheric pressure sensor 230 may operate in a first mode in which the pressure in a first range (e.g., 0 to 2048 hPa) is measured in a first unit (e.g., 0.01 hPa) and in a second mode in which the pressure in a second range (e.g., 6000 to 11000 hPa) is measured in a second unit (e.g., 10 hPa). The atmospheric pressure and the water pressure to the depth of 1 meter may be measured in the first mode, and the water pressure to the depth of 50 meters to 100 meters may be measured in the second mode. The pressure sensor 230 may be the atmospheric pressure sensor capable of measuring the pressure in the first range, and the electronic device 201 may further include another pressure sensor capable of measuring the pressure in the second range.

Figure 6:
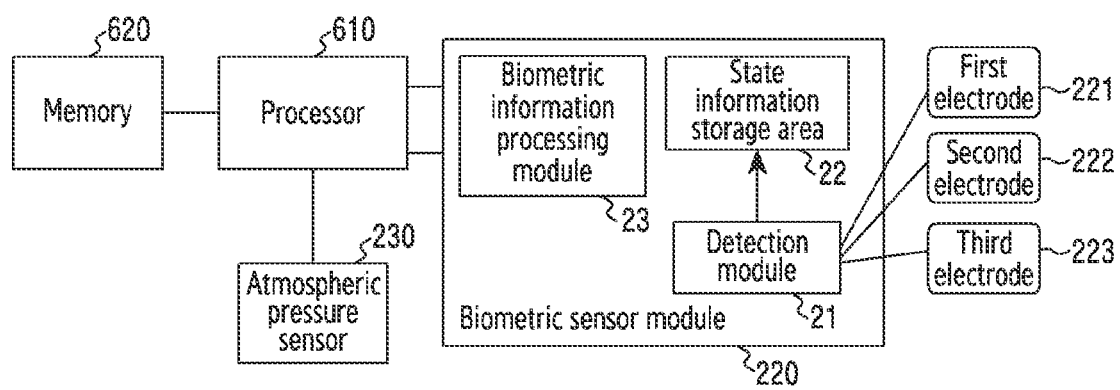
FIG. 6 is a block diagram of an electronic device, according to an embodiment.

FIG. 6 is a block diagram illustrating the configuration of an electronic device, according to an embodiment.

Referring to FIG. 6, an electronic device 601 (e.g., the electronic device 101) may include a processor 610 (e.g., the processor 120 in FIG. 1), a biometric sensor module 220, an atmospheric pressure sensor 230, and a memory 620 (e.g., the memory 130 in FIG. 1).

The biometric sensor module 220 may include a detection module 21, a state information storage area 22, and a biometric information processing module 23. The detection module 21 may detect electrical connections between the first electrode 221, the second electrode 222, and the third electrode 223. The detection module 21 may store information on the detected connection state in the state information storage area 22.

The biometric information processing module 23 may process biometric information detected through at least one of the first electrode 221, the second electrode 222, and the third electrode 223. The biometric information processing module 23 may measure a heart rate, electrocardiogram, body fat/body composition, and/or a stress index through the biometric information detected through at least one of the first electrode 221, the second electrode 222, and the third electrode 223, and may provide the same to the user.

If a context recognition function of the electronic device 601 is turned on (or executed), the detection module 21 may remain in an active state (e.g., always-on). However, the biometric information processing module 23 may be activated only when a function of measuring the biometric information is executed. Thereby, the electronic device 601 in FIG. 6 may reduce current consumption of the biometric sensor module 220 compared to the electronic device 201 in FIG. 3.

Meanwhile, other configurations of the electronic device 601 in FIG. 6 may be similar to those of the electronic device 201 in FIG. 3, so a detailed description thereof will be omitted.

According to an embodiment, an electronic device (e.g., the electronic device 101) may include an atmospheric pressure sensor (e.g., the atmospheric pressure sensor 230) configured to measure pressure, a biometric sensor module (e.g., the biometric sensor module 220) configured to measure biometric information on a user, a processor (e.g., the processor 120, 310) operatively connected to the atmospheric pressure sensor and the biometric sensor module, and a memory (e.g., the memory 130, 320) operatively connected to the processor. The biometric sensor module may include a plurality of electrodes (e.g., the plurality of electrodes 221, 222, 223). Some of the plurality of electrodes may be disposed to come into contact with a body part of the user when the electronic device is worn, and others of the plurality of electrodes may be disposed to not come into contact with a body part of the user when the electronic device is worn. The biometric sensor module may be configured to identify whether a change from a first state, in which the some of the plurality of electrodes are electrically connected, into a second state, in which all of the plurality of electrodes are electrically connected, is detected, identify whether the second state is maintained for a specified first time or more in response to the change into the second state being detected, and transmit an interrupt signal to the processor in response to the second state being maintained for the specified first time or more. The memory may store instructions that, when executed, cause the processor to identify an amount of change in the pressure detected through the atmospheric pressure sensor in response to reception of an interrupt signal, and determine that the electronic device is in a specified first context in response to the amount of change in the pressure being greater than or equal to a specified first threshold.

The memory may store instructions that, when executed, cause the processor to identify whether a change from the second state into the first state is received from the biometric sensor module after the first context is determined, in response to the change into the first state being received, identify whether the amount of change in the pressure detected through the atmospheric pressure sensor is greater than or equal to the first threshold, and determine that the electronic device is in a specified second context in response to the amount of change in the detected pressure being less than the first threshold and the first state and the second state being repeated a specified number of times or more.

The memory may store instructions that, when executed, cause the processor to determine that the electronic device is in a specified third context in response to the amount of change in the detected pressure being greater than or equal to the first threshold.

The memory may store instructions that, when executed, cause the processor to identify whether a pressure greater than or equal to a specified second threshold is maintained for a specified third time or more, and in response to the pressure greater than or equal to the specified second threshold being maintained for the specified third time or more, determine that the electronic device is in a specified fourth context.

The memory may store instructions that, when executed, cause the processor to identify whether the second state is maintained for a specified fourth time or more, and in response to the second state being maintained for the fourth time or more, determine that the electronic device is in a specified fifth context.

The biometric sensor module may be configured to identify whether a change from a third state, in which the plurality of electrodes are not electrically connected to each other, into the second state is detected, and in response to the change from the third state into the second state being detected, transmit an interrupt signal to the processor.

The memory may store instructions that, when executed, cause the processor to execute a specified function or drive a specified mode, based on each context.

The plurality of electrodes may comprise a first electrode (e.g., the first electrode 221) disposed to come into contact with a body part of the user when the electronic device is worn, a second electrode (e.g., the second electrode 222) disposed to come into contact with a body part of the user when the electronic device is worn, and spaced apart from the first electrode, and at least one third electrode (e.g., the third electrode 223) disposed to not come into contact with a body part of the user when the electronic device is worn. The first electrode and the second electrode are disposed on the rear surface of the electronic device. The at least one third electrode is disposed on a side surface or an upper surface of the electronic device.

The biometric sensor module may comprise a detection module (e.g., the detection module 21) configured to detect an electrical connection state between the plurality of electrodes, a state information storage area (e.g., the state information storage area 22) configured to store information corresponding to the detected state, and a biometric information processing module (e.g., the biometric information processing module 23) configured to process the biometric information detected using at least some of the plurality of electrodes.

The biometric information processing module may be activated while the biometric information is measured, and be deactivated while context recognition is executed.

According to an embodiment, an electronic device (e.g., the electronic device 101) may include an atmospheric pressure sensor (e.g., the atmospheric pressure sensor 230) configured to measure pressure, a biometric sensor module (e.g., the biometric sensor module 220) configured to measure biometric information on a user, a processor (e.g., the processor 120, 310) operatively connected to the atmospheric pressure sensor and the biometric sensor module, and a memory (e.g., the memory 130, 320) operatively connected to the processor. The biometric sensor module may include a plurality of electrode (e.g., the plurality of electrodes 221, 222, 223). Some of the plurality of electrodes may be disposed to come into contact with a body part of the user when the electronic device is worn, and others of the plurality of electrodes may be disposed to not come into contact with a body part of the user when the electronic device is worn. The biometric sensor module may be configured to be activated in response to a wake-up signal being received from the processor, identify whether a state in which the plurality of electrodes are electrically connected is maintained for a specified first time or more, and transmit an interrupt signal to the processor in response to the state being maintained for the specified first time or more. The memory may store instructions that, when executed, cause the processor to transmit the wake-up signal to the biometric sensor module in response to an amount of change in the pressure measured through the atmospheric pressure sensor being greater than or equal to a specified first threshold, and determine that the electronic device is in a specified first context in response to reception of an interrupt signal from the biometric sensor module.

The memory may store instructions that, when executed, cause the processor to identify whether a change into another state in which a first electrode (e.g., the first electrode 221) and a second electrode (e.g., the second electrode 222) are electrically connected is received from the biometric sensor module after the first context is determined, in response to the change into the another state being received, identify whether the amount of change in the pressure detected through the atmospheric pressure sensor is greater than or equal to the first threshold, and determine that the electronic device is in a specified second context, in response to the amount of change in the pressure detected after the change into the another state is received being less than the first threshold and the state and the another state being repeated a specified number of times or more.

The memory may store instructions that, when executed, cause the processor to determine that the electronic device is in a specified third context in response to the amount of change in the detected pressure being greater than or equal to the first threshold after the change into the another state is received.

The memory may store instructions that, when executed, cause the processor to identify whether a pressure greater than or equal to a specified second threshold is maintained for a specified third time or more, and in response to the pressure greater than or equal to the specified second threshold being maintained for the specified third time or more, determine that the electronic device is in a specified fourth context.

The memory may store instructions that, when executed, cause the processor to identify whether the state is maintained for a specified fourth time or more, and in response to the state being maintained for the fourth time or more, determine that the electronic device is in a specified fifth context.

The memory may further store instructions that cause, when executed, the processor to execute a specified function or drive a specified mode, based on each context.

Hereinafter, for convenience of description, embodiments in FIGS. 7 to 15 will be described based on the configuration of the electronic device 201 described with reference to FIG. 3, by way of example. However, it will be obvious to those skilled in the art that the embodiments in FIGS. 7 to 15 are able to be applied to the electronic device 601 in FIG. 6 in the same manner.

Figure 7:
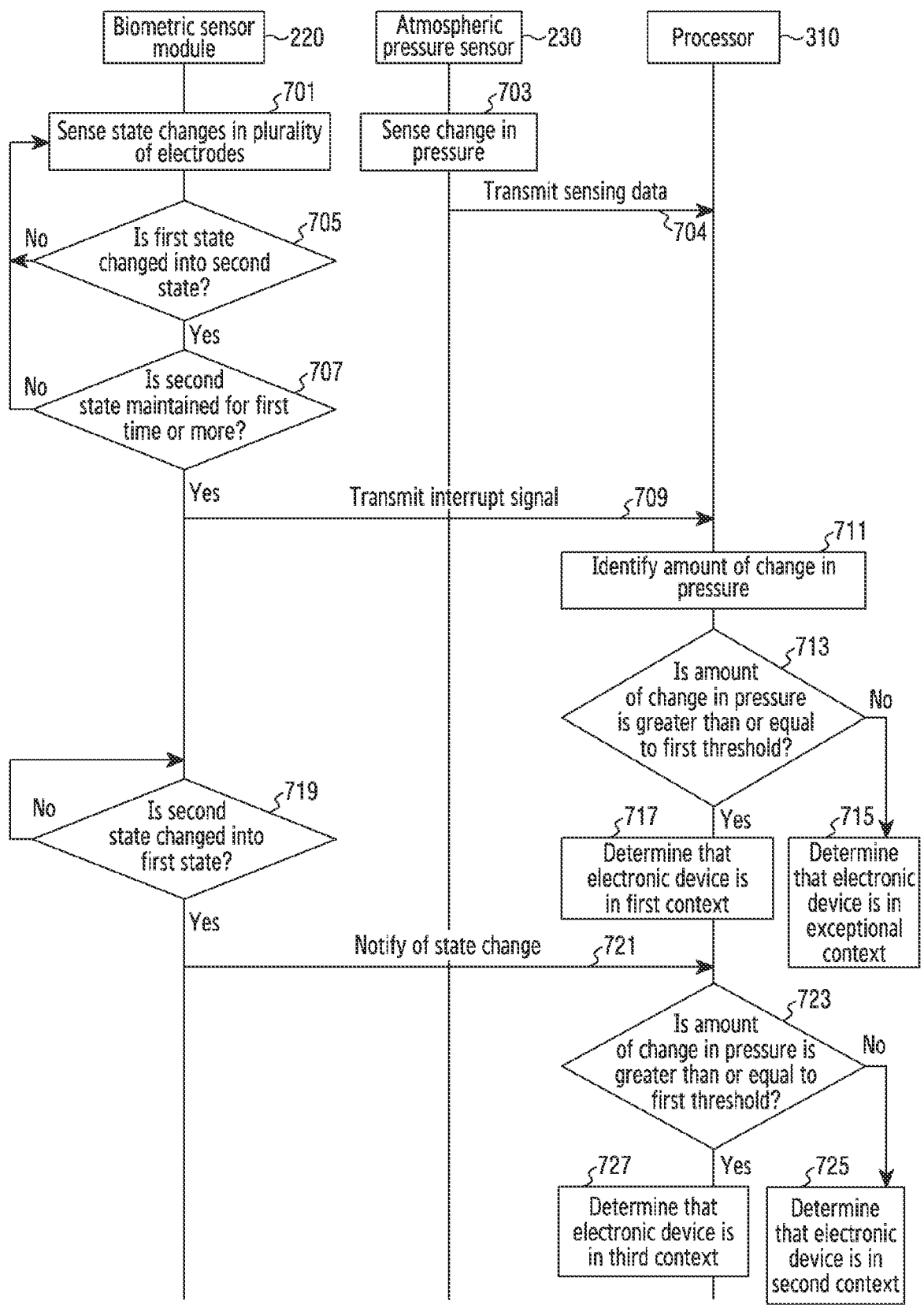
FIG. 7 is a flowchart illustrating a method of recognizing a context of an electronic device, according to an embodiment.
Figure 8A:
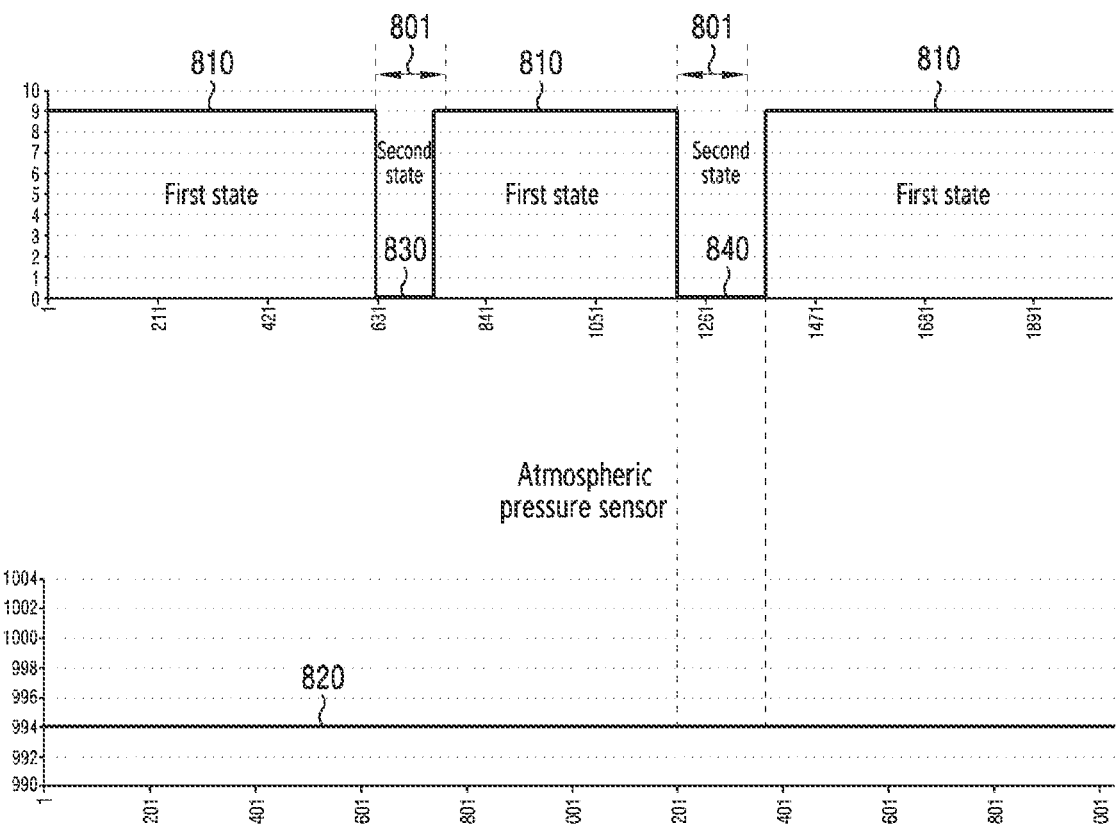
FIG. 8A is a graph showing changes in a biometric sensor module and an atmospheric pressure sensor when an electronic device is located outside water, according to an embodiment.
Figure 8B:
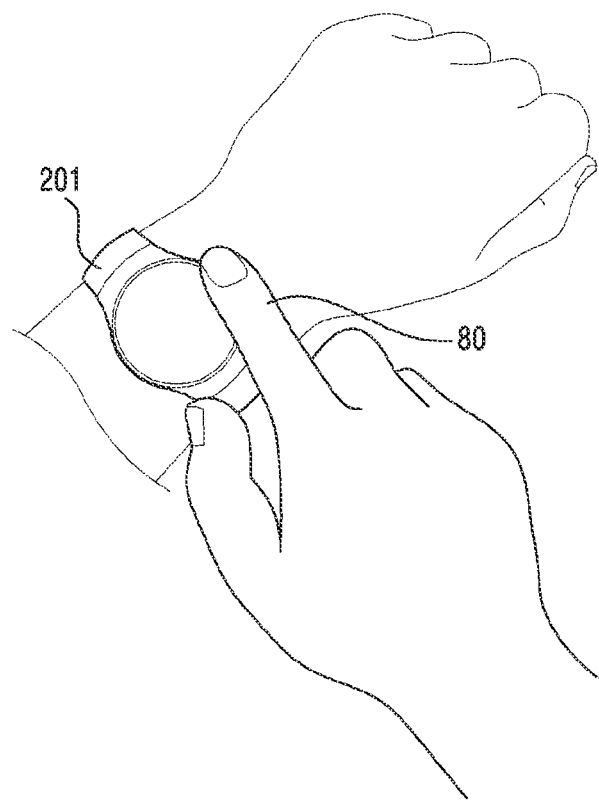
FIG. 8B is a diagram illustrating an example of an exceptional context in which a user of an electronic device touches a third electrode of a biometric sensor module, according to an embodiment.
Figure 9A:
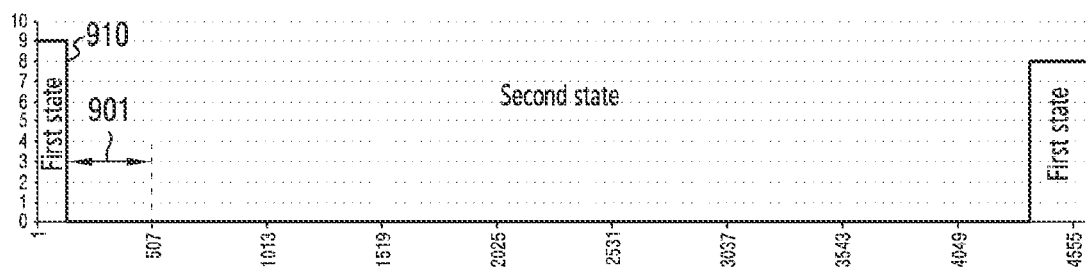
FIG. 9A is a graph showing changes in a biometric sensor module and an atmospheric pressure sensor when an electronic device enters the water, according to an embodiment.
Figure 9A:
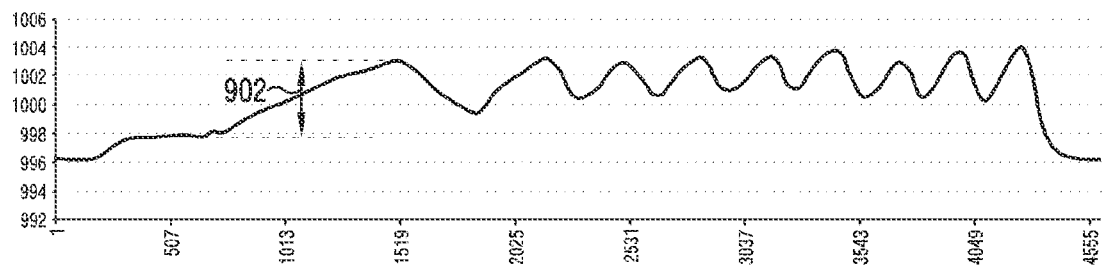
Figure 9B:
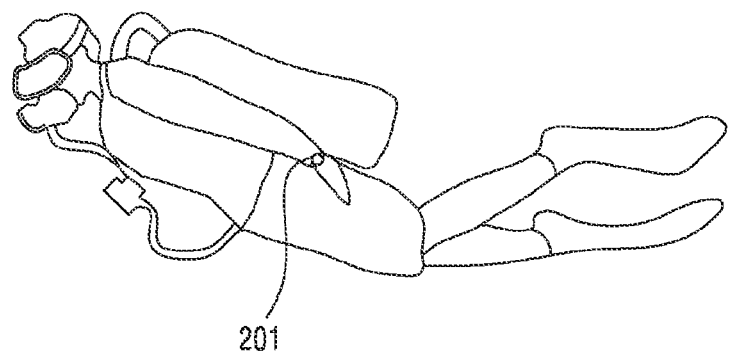
FIG. 9B is a diagram illustrating an example of a first context in which a user of an electronic device is underwater, according to an embodiment.
Figure 10A:
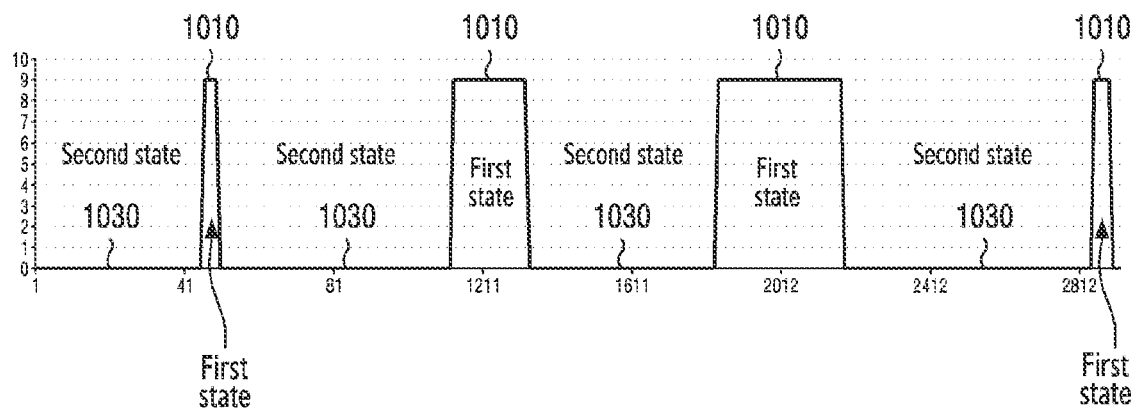
FIG. 10A is a graph showing changes in a biometric sensor module and an atmospheric pressure sensor when a user of an electronic device swims, according to an embodiment.
Figure 10A:
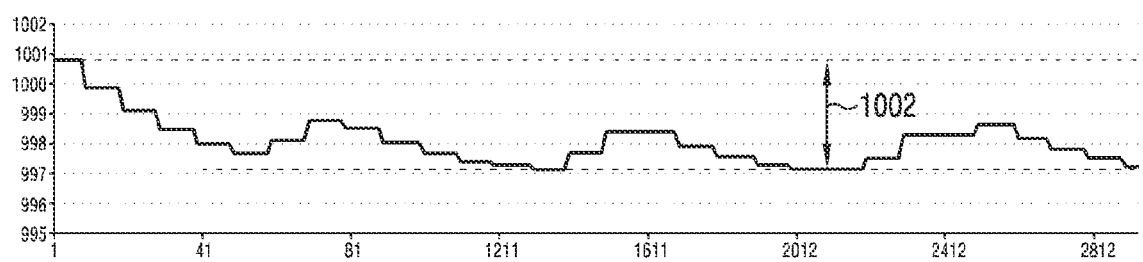
Figure 10B:
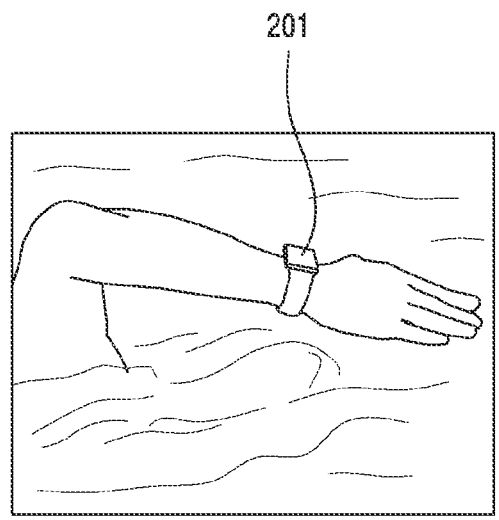
FIG. 10B is a diagram illustrating an example of a second context in which a user of an electronic device swims, according to an embodiment.
Figure 11:
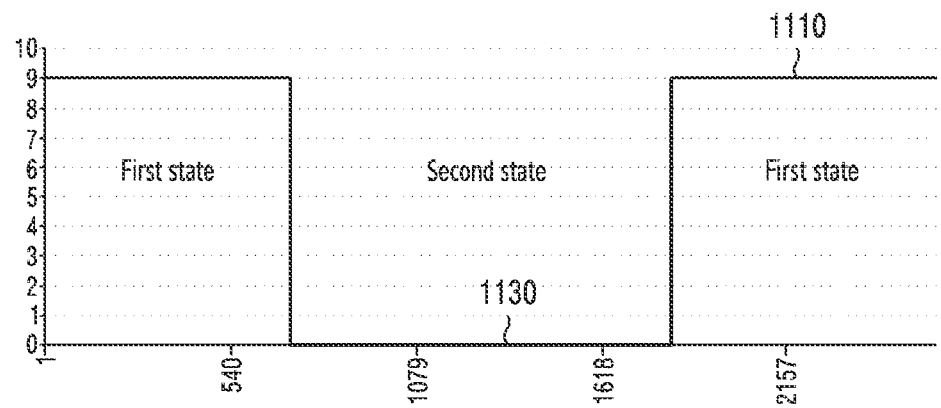
FIG. 11 is a graph showing changes in a biometric sensor module and an atmospheric pressure sensor when an electronic device comes out of the water, according to an embodiment.
Figure 11:
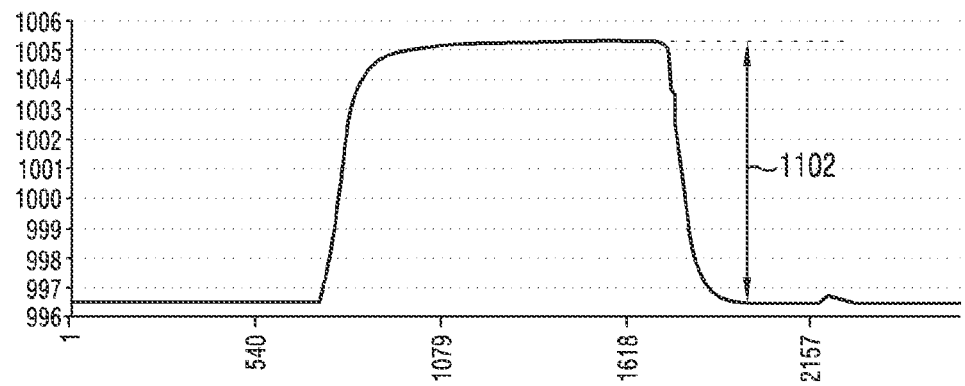
Figure 12A:
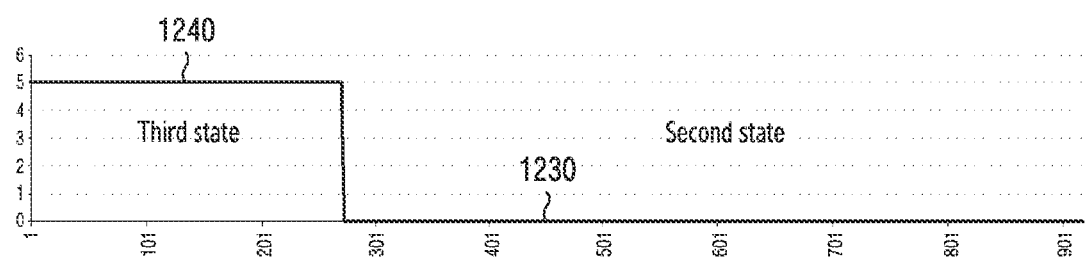
FIG. 12A is a graph showing changes in a biometric sensor module and an atmospheric pressure sensor when an electronic device is worn on clothing, according to an embodiment.
Figure 12A:
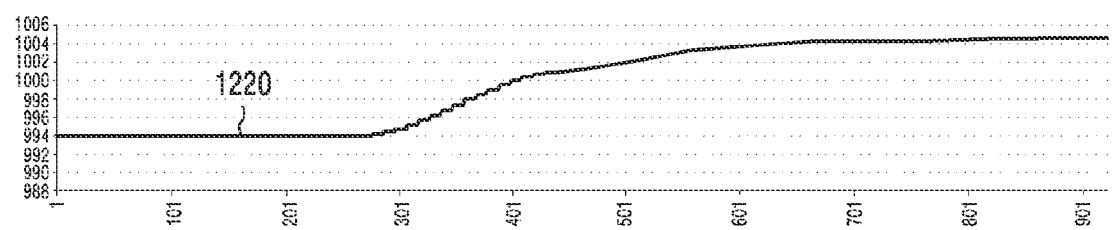
Figure 12B:
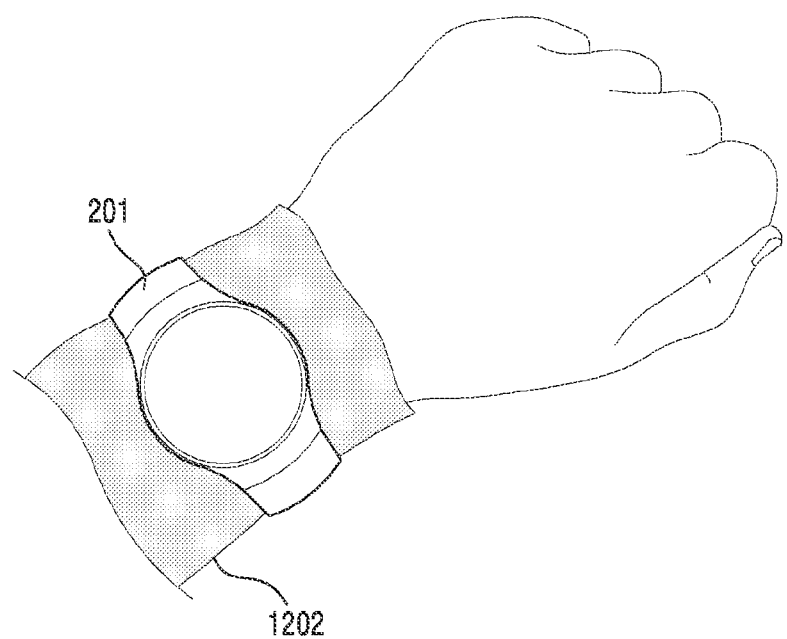
FIG. 12B is a diagram illustrating an example of wearing an electronic device on clothing, according to an embodiment.

FIG. 7 is a flowchart illustrating a method of recognizing a context of an electronic device, according to an embodiment. FIG. 8A is a graph showing changes in a biometric sensor module and an atmospheric pressure sensor when an electronic device is located outside water, according to an embodiment. FIG. 8B is a diagram illustrating an example of an exceptional context in which a user of an electronic device touches a third electrode of a biometric sensor module, according to an embodiment. FIG. 9A is a graph showing changes in a biometric sensor module and an atmospheric pressure sensor when an electronic device enters the water, according to an embodiment. FIG. 9B is a diagram illustrating an example of a first context in which a user of an electronic device is underwater, according to an embodiment. FIG. 10A is a graph showing changes in a biometric sensor module and an atmospheric pressure sensor when a user of an electronic device swims, according to an embodiment. FIG. 10B is a diagram illustrating an example of a second context in which a user of an electronic device swims, according to an embodiment. FIG. 11 is a graph showing changes in a biometric sensor module and an atmospheric pressure sensor when an electronic device comes out of the water, according to an embodiment. FIG. 12A is a graph showing changes in a biometric sensor module and an atmospheric pressure sensor when an electronic device is worn on clothing, according to an embodiment. FIG. 12B is a diagram illustrating an example of wearing an electronic device on clothing, according to an embodiment.

Prior to a detailed description, the state information graphs of the biometric sensor module shown in FIGS. 8A, 9A, 10A, 11, and 12A may indicate a change in the state information of a biometric sensor module, which is determined based on the electrical connection state of a plurality of electrodes (e.g., the first electrode 221, the second electrode 222, and the third electrode 223) of the biometric sensor module, as shown in Table 1 above. Values on the Y-axis of the state information graph are examples of the flag values indicating state information, and do not represent sensing values of the biometric sensor module.

Referring to FIGS. 7 to 12B, the biometric sensor module 220 of an electronic device 201 (e.g., the electronic device 101) may sense state changes of a plurality of electrodes 221, 222, and 223 at operation 701. When the electronic device 201 is worn on a body part (e.g., a wrist) of the user, the biometric sensor module 220 may obtain a first state 810 in which the first electrode 221 and the second electrode 222 are electrically connected through the body of the user.

The atmospheric pressure sensor 230 may sense a change in atmospheric pressure at operation 703, and may transmit sensing data thereon to the processor 310 at operation 704.

The atmospheric pressure sensor 230 may periodically transmit the sensing data to the processor 310. In this case, the processor 310 may store the sensing data in a memory (e.g., the memory 130 or the memory 320) (or a buffer memory). The atmospheric pressure sensor 230 may have a specific pressure value when the electronic device 201 stays in the atmosphere, as denoted by reference numeral 820 in FIG. 8A.

At operation 705, the biometric sensor module 220 may identify whether or not the first state is changed into a second state. Here, the second state may be the state in which the first electrode 221, the second electrode 222, and the third electrode 223 are electrically connected.

As a result of the identification at operation 705, if the first state is not changed into the second state, the biometric sensor module 220 may return to operation 701. On the other hand, if the first state is changed into the second state as a result of the identification at operation 705, the biometric sensor module 220 may identify whether or not the second state is maintained for a specified first time 801 (e.g., 1 second) or more at operation 707.

As a result of the identification at operation 707, if the second state is not maintained for the first time 801 or more, the biometric sensor module 220 may return to operation 701. As shown in FIG. 8B, if the user temporarily touches the third electrode 223 (e.g., for less than the first time 801) using a finger 80 of the hand opposite the hand on which the electronic device 201 is worn, the biometric sensor module 220 may temporarily change into the second state, and may then return to the first state, as denoted by reference numeral 830 in FIG. 8A. On the other hand, if the second state is maintained for the first time 801 or more as a result of the identification at operation 707, the biometric sensor module 220 may transmit an interrupt signal to the processor 310 at operation 709. The processor 310 may receive the interrupt signal in an active state or in an inactive state. The processor 310 in the inactive state may be activated in response to reception of the interrupt signal. In response to the reception of the interrupt signal, the processor 310 may identify state information stored in a register, and may determine whether or not the electronic device 201 enters the water, based on the identified result.

At operation 711, the processor 310 may identify the amount of change in pressure. The processor 310 may identify the amount of change in the pressure detected through the atmospheric pressure sensor 230 from the time at which the interrupt signal is received. The processor 310 may identify the amount of change in the pressure from the time before the interrupt signal is received (e.g., before the first time 801). To this end, the atmospheric pressure sensor 230 may store pressure values measured during a predetermined time (e.g., the first time 801 or more) in a specified area (e.g., the memory 320 or a buffer memory), and the processor 310 may identify a change in the pressure through the stored pressure values.

At operation 713, the processor 310 may identify whether or not the amount of change in the pressure is greater than or equal to a specified first threshold (e.g., 8 hPa). The processor 310 may identify whether or not the amount of change in the pressure within a specified second time (e.g., 3 seconds) is greater than or equal to the specified first threshold (e.g., 8 hPa). As a result of the identification at operation 713, if the amount of change in the pressure is less than the first threshold, the processor may determine that the electronic device is in an exceptional context at operation 715. As denoted by reference numeral 840 in FIG. 8A, even if the biometric sensor module 220 maintains the second state for the first time period 801 or more, if there is no change in the pressure detected through the atmospheric pressure sensor 230, the processor 310, as shown in FIG. 8B, may determine that the electronic device is in the exceptional context in which the user touches the third electrode 223 using the finger 80 for the first time period 801 or more.

On the other hand, as a result of the identification at operation 713, if the amount of change in the pressure is greater than or equal to the first threshold, the processor may determine that the electronic device is in a first context at operation 717. As shown in FIG. 9A, if the second state is maintained for a predetermined time 901 after the biometric sensor module 220 changes 910 from the first state into the second state, and if the amount of change in the pressure 902 detected through the atmospheric pressure sensor 230 exceeds the first threshold, the processor 310 may determine that the user has entered the water while wearing the electronic device 201 as shown in FIG. 9B.

At operation 719, the biometric sensor module 220 may identify whether or not the second state is changed into the first state. As a result of the identification at operation 719, if the second state is not changed into the first state, the biometric sensor module 220 may maintain at operation 719. On the other hand, if the second state is changed into the first state as a result of the identification at operation 719, the biometric sensor module 220 may notify the processor 310 of the state change at operation 721.

At operation 723, the processor 310 may identify whether or not the amount of change in the pressure is greater than or equal to the first threshold. If the amount of change in the pressure is less than the first threshold as a result of the identification at operation 723, the processor 310 may determine that the electronic device is in a second context at operation 725. The processor 310 may determine that the user is swimming.

According to some embodiments, as shown in FIG. 10A, if a change from the second state 1030 into the first state 1010 is repeated a predetermined number of times or more, and if the change in the pressure 1002 (about 4 hPa) is less than the first threshold (e.g., 8 hPa), the processor 310 may determine that the user is swimming while wearing the electronic device 201 as shown in FIG. 10B.

As a result of the identification at operation 723, if the amount of change in the pressure is greater than or equal to the first threshold, the processor 310 may determine that the electronic device is in a third context at operation 727. As shown in FIG. 11, if the biometric sensor module 220 changes from the second state 1130 to the first state 1110, and if a change in the pressure 1102 is greater than or equal to the first threshold, the processor 310 may determine that the user of the electronic device 201 has come out of the water.

Meanwhile, although it is identified whether or not the biometric sensor module 220 changes from the first state into the second state at operation 705 in FIG. 7, the biometric sensor module 220, as shown in FIG. 12A, may identify whether or not a third state 1240, in which none of the first electrode 221, the second electrode 222, and the third electrode 223 is electrically connected, into the second state 1230. This is due to the fact that in the case where the user wears clothing 1202 with long sleeves and wears the electronic device 201 on the clothing 1202 as shown in FIG. 12B, although the electronic device 201 is worn on the body part of the user, the first electrode 221 and the second electrode 222 of the biometric sensor module 220 may not be electrically connected due to the non-conductive clothing 1202.

If the user enters the water, as shown in FIG. 12A, the first electrode 221, the second electrode 222, and the third electrode 223 may be electrically connected by the water so that the biometric sensor module 220 may change from the third state 1240 into the second state 1230, and so that the pressure detected through the atmospheric pressure sensor 230 may also increase above the first threshold.

If the second state is maintained for a specified fourth time (e.g., 1 hour) or more, the processor 310 may determine that the electronic device 201 is in a fifth context (e.g., loss). This is due to the fact that the user rarely stays in the water for the fourth time or more and that even if the user stays in the water for more than the fourth time, the electronic device 201 is likely to be exposed temporarily (or momentarily) out of the water and then switch to the first state. However, if the user drops the electronic device 201 into the water while carrying the electronic device without wearing the same, or if the electronic device 201 is released from the body while entering the water, the second state may be maintained for the fourth time or more. In this case, the processor 310 may determine that the electronic device is in the fifth context (loss).

The processor 310 may execute a function (mode) according to the recognized context. If the first context (e.g., entry into the water) is recognized, the processor 310 may activate various sensors for determining the type of underwater activity. If the second context (e.g., swimming) is recognized, the processor 310 may drive an algorithm for determining the swimming stroke (e.g., freestyle, breaststroke, butterfly, or diving). The processor 310 may activate a GPS module to measure and/or store information on the active area and/or distance (e.g., swimming distance). If the third context (e.g., out of water) is recognized, the processor 310 may return to a normal state. If the fourth context (e.g., deep dive) is recognized, the processor 310 may switch the mode of the atmospheric pressure sensor, or may activate the atmospheric pressure sensor capable of measuring the pressure in the second range, thereby providing water depth information. Alternatively, when providing water depth information, the processor 310 may change the brightness of the display, or may change a user interface (UI) (e.g., font size and/or color) for improving visibility. If the fifth context (e.g., loss) is recognized, the processor 310 may notify of a loss context of the electronic device 201, and may output a specified sound effect or emit specified light in order to expose the location of the electronic device 201.

Figure 13:
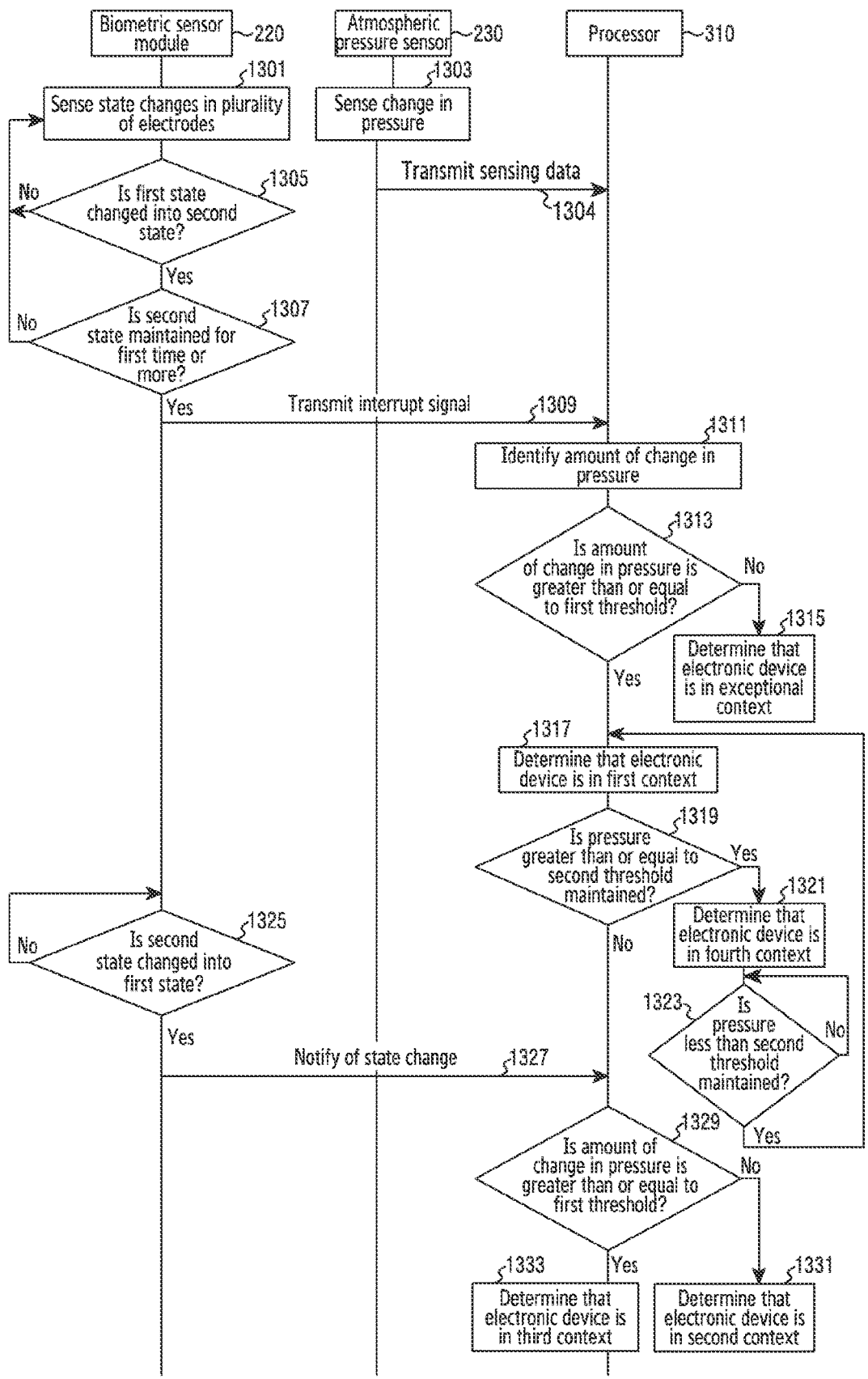
FIG. 13 is a flowchart illustrating a method of recognizing a context of an electronic device, according to an embodiment.
Figure 14:
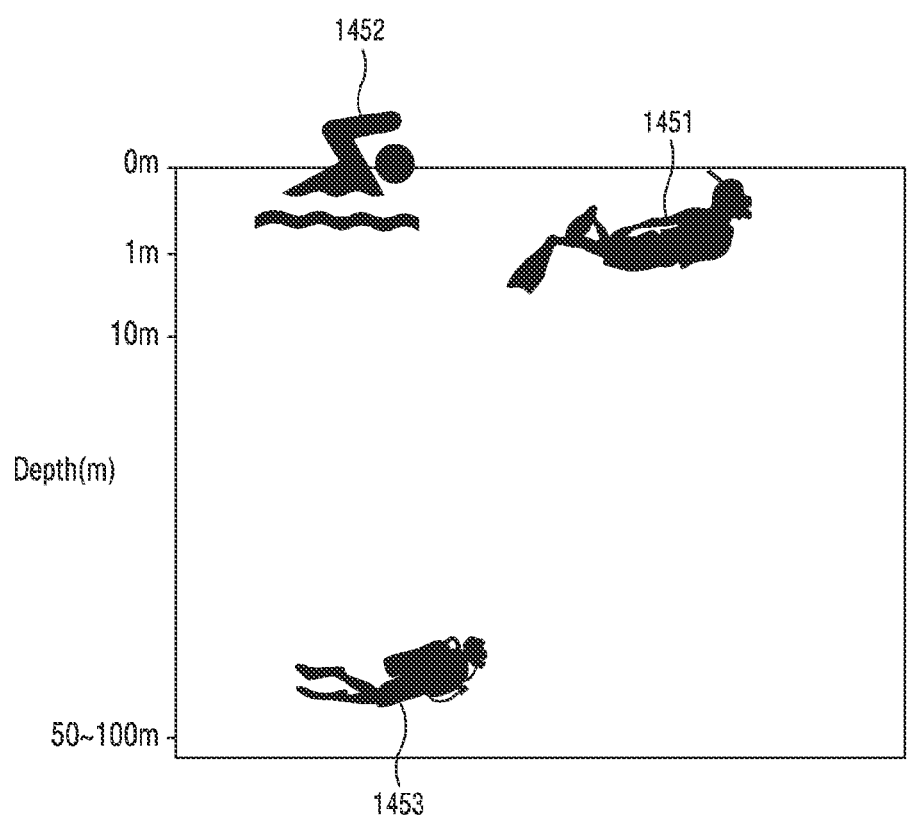
FIG. 14 is an exemplary diagram illustrating underwater contexts of an electronic device, according to an embodiment.

FIG. 13 is a flowchart illustrating a method of recognizing a context of an electronic device, according to an embodiment. FIG. 14 is an exemplary diagram illustrating contexts of an electronic device, according to an embodiment.

Operations 1301 to 1317 in FIG. 13 may be the same as or similar to operations 701 to 717 in FIG. 7, so a detailed description thereof will be omitted.

At operation 1319, the processor 310 may identify whether or not a pressure greater than or equal to a specified second threshold (e.g., 2048 hPa) is maintained for a specified third time or more. The second threshold may be the pressure value at a specified water depth (e.g., 1 meter).

As a result of the identification at operation 1319, if the pressure greater than or equal to the second threshold is not maintained for the third time or more, the processor 310 may proceed to operation 1329. On the other hand, as a result of the identification at operation 1319, if the pressure greater than or equal to the second threshold is maintained for the third time or more, the processor 310 may determine that the electronic device is in a fourth context at operation 1321. The processor 310 may determine the electronic device is in a context in which the user wears the electronic device 201 and dives into the water 1 meter deep. If the fourth context is determined, the processor 310 may switch the mode of the atmospheric pressure sensor 230 from the first mode to the second mode. The processor 310 may deactivate the atmospheric pressure sensor capable of measuring the pressure in the first range, and may activate a pressure sensor capable of measuring the pressure in the second range.

The processor 310, at operation 1323, may identify whether or not a pressure less than the second threshold is maintained for the third time or more. As a result of the identification at operation 1323, if the pressure less than the second threshold is not maintained for the third time or more, the processor 310 may maintain at operation 1323. On the other hand, as a result of the identification at operation 1323, if the pressure less than the second threshold is maintained for the third time or more, the processor 310 may proceed to operation 1317. The processor 310 may switch the mode of the atmospheric pressure sensor 230 from the second mode to the first mode. The processor 310 may deactivate the pressure sensor, and may activate the atmospheric pressure sensor 230.

Operations 1325 to 1333 in FIG. 13 may be the same as or similar to Operations 719 to 727 in FIG. 7, so a detailed description thereof will be omitted.

As shown in FIG. 14, the electronic device 201 may recognize various underwater contexts through the biometric sensor module 220 and the atmospheric pressure sensor 230. The electronic device 201 may recognize whether the electronic device 201 is located in shallow water 1451 within a first range, the user thereof is swimming 1452, the electronic device 201 is located in deep water 1453 within a second range, or is located out of water through the biometric sensor module 220 and the atmospheric pressure sensor 230.

Figure 15:
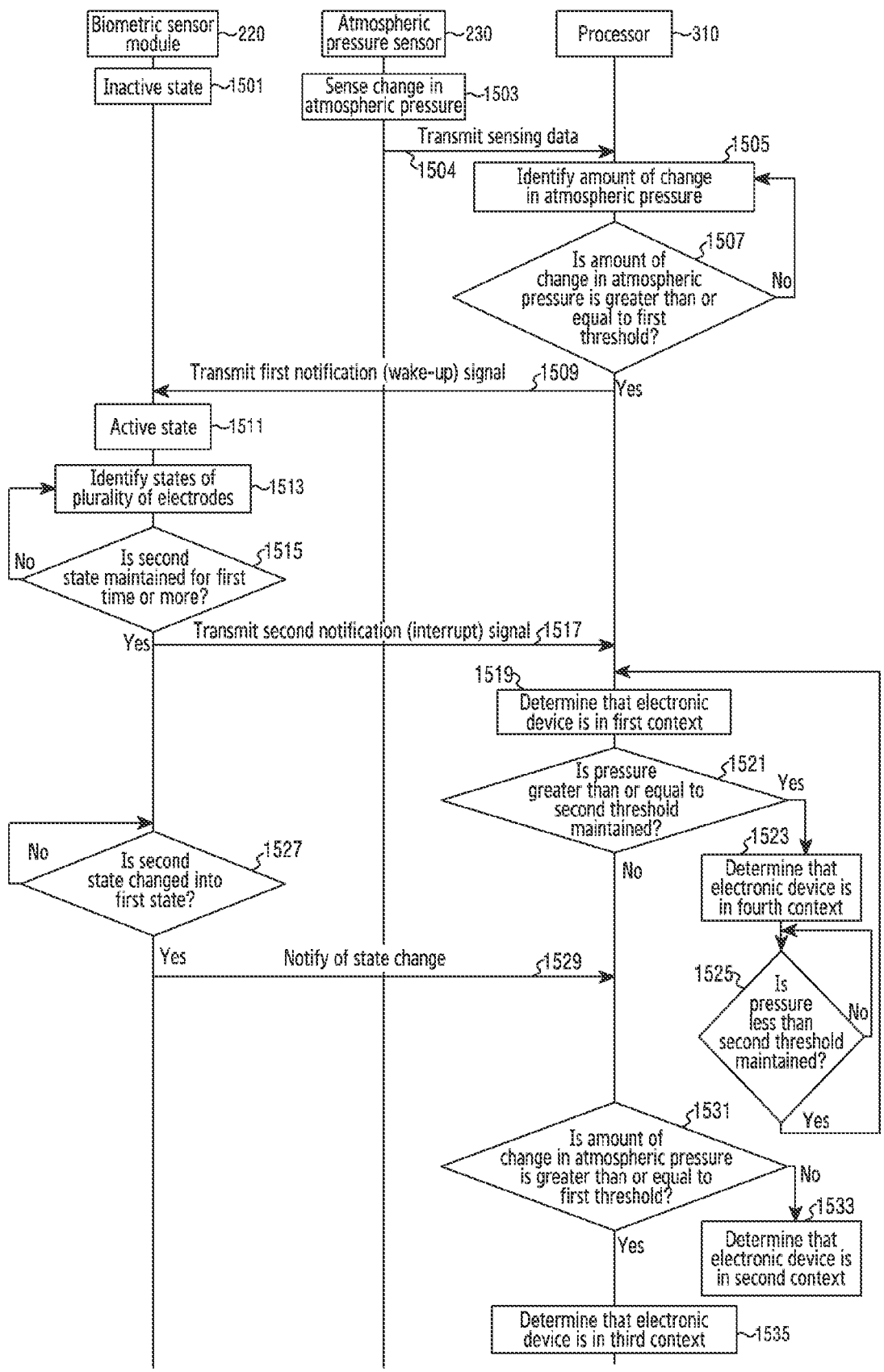
FIG. 15 is a flowchart illustrating a method of recognizing a context of an electronic device, according to an embodiment.

FIG. 15 is a flowchart illustrating a method of recognizing a context of an electronic device, according to an embodiment.

Referring to FIG. 15, at operation 1501, the biometric sensor module 220 of the electronic device 201 may be in an inactive state. The atmospheric pressure sensor 230 may sense a change in pressure at operation 1503, and may transmit sensing data thereon to the processor 310 at operation 1504. The atmospheric pressure sensor 230 may periodically sense the pressure, and may transmit the same to the processor 310. The processor 310 may store the sensing data in a specified area (e.g., a partial area of the memory 320).

The processor 310 may identity the amount of change in pressure at operation 1505. At operation 1507, the processor 310 may identify whether or not the amount of change in pressure is greater than or equal to a specified first threshold (e.g., 8 hPa). As a result of the identification at operation 1507, if the amount of change in pressure is less than the first threshold, the processor 310 may return to operation 1505. On the other hand, if the amount of change in pressure is greater than or equal to the first threshold as a result of the identification at operation 1507, the processor 310 may transmit a first notification signal (e.g., a wake-up signal) to the biometric sensor module 220 at operation 1509. The biometric sensor module 220 may be activated at operation 1511.

The biometric sensor module 220 may identify the states of a plurality of electrodes at operation 1513. The biometric sensor module 220 may identify whether or not a first electrode (e.g., the first electrode 221), a second electrode (e.g., the second electrode 222), and a third electrode (e.g., the third electrode 223) are in a second state in which they are electrically connected.

The biometric sensor module 220 may identity whether or not the second state is maintained for a first time or more at operation 1515. As a result of the identification at operation 1515, if the second state is not maintained for the first time or more, the biometric sensor module 220 may return to operation 1513. On the other hand, if the second state is maintained for the first time or more as a result of the identification at operation 1515, the biometric sensor module 220 may transmit a second notification signal (e.g., an interrupt signal) to the processor 310 at operation 1517.

Operations 1519 to 1535 in FIG. 15 are the same as or similar to operations 1317 to 1333 in FIG. 13, so a detailed description thereof will be omitted.

The electronic device 201 described above is able to reduce current consumption, compared to the embodiments described with reference to in FIGS. 7 and 13, because the biometric sensor module 220 is activated when a change in pressure greater than or equal to the first threshold is detected through the atmospheric pressure sensor 230.

Figure 16:
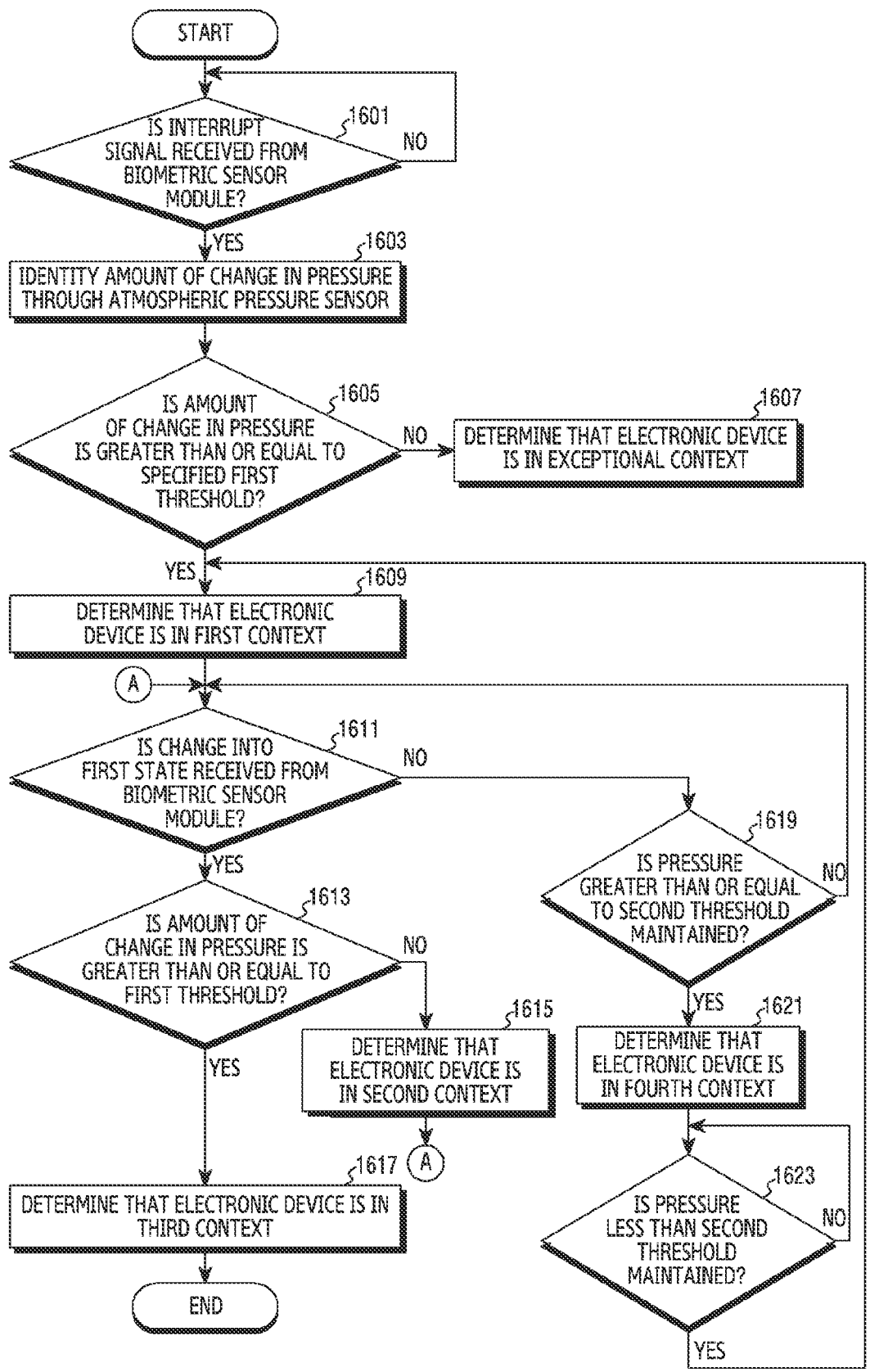
FIG. 16 is a flowchart illustrating a method of recognizing a context of an electronic device, according to an embodiment.

FIG. 16 is a flowchart illustrating a method of recognizing a context of an electronic device, according to an embodiment.

Referring to FIG. 16, a processor (e.g., the processor 120, the processor 310, or the processor 610) of an electronic device (e.g., the electronic device 101, 201, or 601) may identity whether or not an interrupt signal is received from a biometric sensor module (e.g., the biometric sensor module 220) at operation 1601. After the electronic device is worn on a body part (e.g., a wrist) of the user, the processor may identity whether or not the interrupt signal is received from the biometric sensor module in an active state or an inactive state of the electronic device. If a first electrode (e.g., the first electrode 221), a second electrode (e.g., the second electrode 222), and a third electrode (e.g., the third electrode 223) included in the biometric sensor module are electrically connected for a specified first time (e.g., 1 second) or more, the interrupt signal may be transmitted to the processor by the biometric sensor module.

As a result of the identification at operation 1601, if the interrupt signal is not received, the processor may maintain at operation 1601. On the other hand, if the interrupt signal is received as a result of the identification at operation 1601, the processor may identity the amount of change in pressure through an atmospheric pressure sensor (e.g., the atmospheric pressure sensor 230) at operation 1603. The processor may identity the amount of change in the pressure sensed through the atmospheric pressure sensor from the time at which the interrupt signal is received. The processor may identity the amount of change in pressure from the time before receiving the interrupt signal (e.g., the time at which the biometric sensor module switches to the second state). To this end, the atmospheric pressure sensor may store the pressure measured for a predetermined time (e.g., the time exceeding the first time) in a specified area (e.g., the memory 130, the memory 320, or a buffer memory)).

The processor may identity whether or not the amount of change in pressure is greater than or equal to a specified first threshold (e.g., 8 hPa) at operation 1605. The processor may identity whether or not the amount of change in pressure within a specified second time (e.g., 3 seconds) is greater than or equal to the specified first threshold.

As a result of the identification at operation 1605, if the amount of change in pressure is less than the first threshold, the processor may determine that the electronic device is in an exceptional context at operation 1607. The processor may determine that the electronic device is in a context in which the user is touching the third electrode using a finger outside the water. On the other hand, as a result of the identification at operation 1605, if the amount of change in pressure is greater than or equal to the first threshold, the processor may determine that the electronic device is in a first context at operation 1609. The processor may determine that the electronic device is in a context in which the electronic device is underwater.

The processor may identity whether or not a notification signal indicating a change into the first state is received from the biometric sensor module at operation 1611. If the notification signal is received as a result of the identification at operation 1611, the processor may determine whether or not the amount of change in pressure is greater than or equal to the first threshold at operation 1613. The processor may identify whether or not the amount of change in pressure within a second time is greater than or equal to the specified first threshold.

As a result of the identification at operation 1613, if the amount of change in pressure is less the first threshold, the processor may determine that the electronic device is in a second context at operation 1615. The processor may determine that the electronic device is in a context in which the user is swimming. If the first state and the second state are repeated a predetermined number of times (e.g., three times) or more, the processor may determine that the electronic device is in the second context.

On the other hand, as a result of the identification at operation 1613, if the amount of change in pressure is greater than or equal to the first threshold, the processor may determine that the electronic device is in a third context at operation 1617. The processor may determine that the electronic device is in a context in which the user stays out of the water.

If the notification signal is not received as a result of the identification at operation 1611, the processor may identify whether or not a pressure greater than or equal to the specified second threshold is maintained at operation 1619. The processor may identify whether or not the pressure greater than or equal to the second threshold is maintained for a third time or more.

As a result of the identification at operation 1619, if the pressure greater than or equal to the second threshold is not maintained, the processor may return to operation 1611. On the other hand, as a result of the identification at operation 1619, if the pressure greater than or equal to the second threshold is maintained, the processor may determine that the electronic device is in a fourth context at operation 1621. The processor may determine that the electronic device is in a context in which the user dived underwater to a specified depth (e.g., 1 meter). If the fourth context is determined, the processor may switch the mode of the atmospheric pressure sensor from a first mode to a second mode. The processor may deactivate the atmospheric pressure sensor capable of measuring the pressure in a first range, and may activate a pressure sensor capable of measuring the pressure in a second range.

The processor may identify whether or not a pressure less than the second threshold is maintained at operation 1623. The processor may identify whether or not the pressure less than the second threshold is maintained for a third time or more.

As a result of the identification at operation 1623, if the pressure less than the second threshold is not maintained, the processor may maintain at operation 1623. On the other hand, as a result of the identification at operation 1623, if the pressure less than the second threshold is maintained, the processor may return to operation 1609. The processor may determine that the electronic device has moved from below the specified depth (e.g., 1 meter) to above the specified depth. The processor may switch the mode of the atmospheric pressure sensor from the second mode to the first mode. The processor may deactivate the pressure sensor, and may activate the atmospheric pressure sensor.

Figure 17:
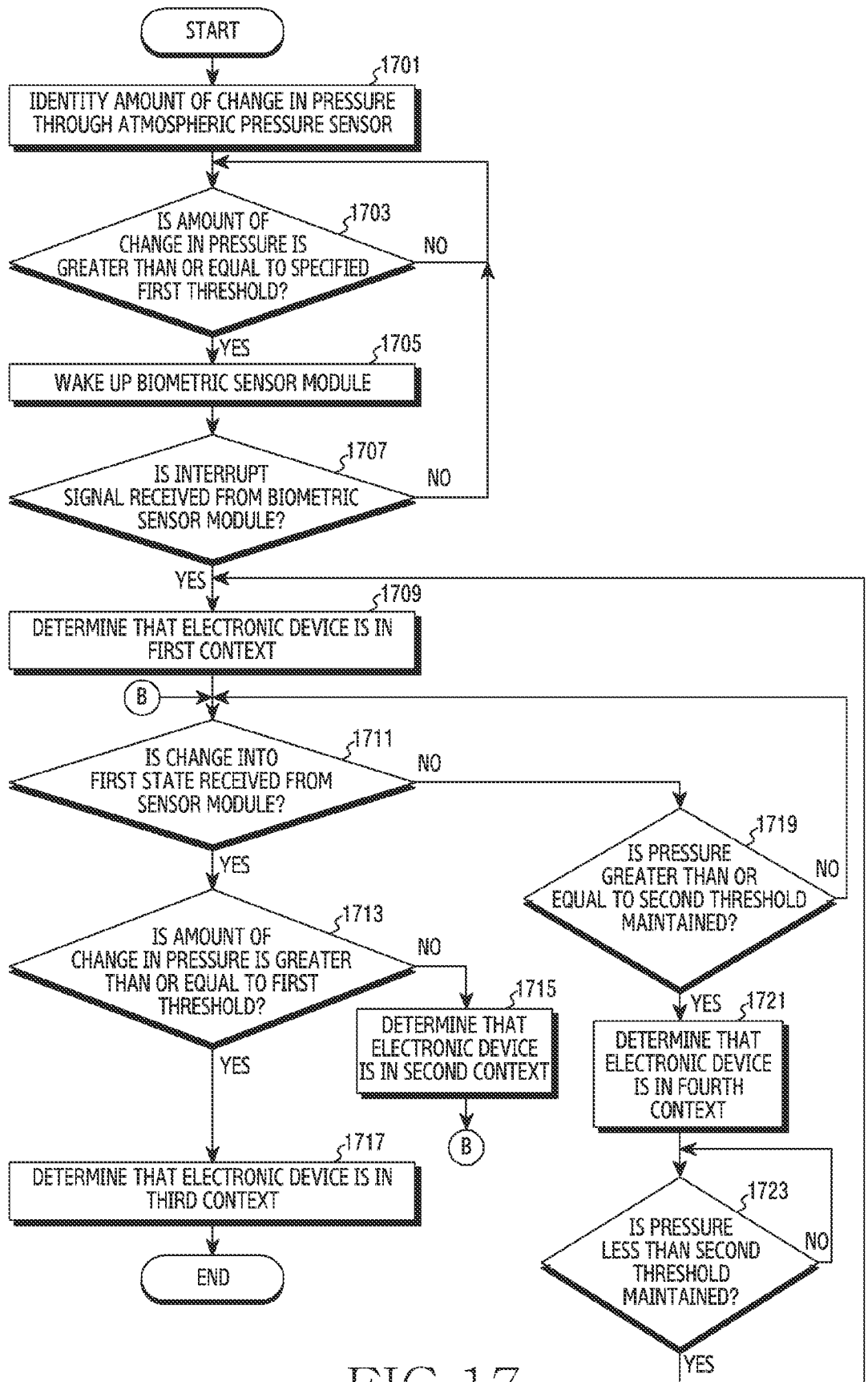
FIG. 17 is a flowchart illustrating a method of recognizing a context of an electronic device, according to an embodiment.

FIG. 17 is a flowchart illustrating a method of recognizing a context of an electronic device, according to an embodiment.

Referring to FIG. 17, a processor (e.g., the processor 120, the processor 310, or the processor 610) of an electronic device (e.g., the electronic device 101, 201, or 601) may identify the amount of change in pressure through an atmospheric pressure sensor (e.g., the atmospheric pressure sensor 230) at operation 1701.

The processor may identify whether or not the amount of change in pressure is greater than or equal to a specified first threshold (e.g., 8 hPa) at operation 1703. The processor may identify whether or not the amount of change in pressure within a specified second time (e.g., 3 seconds) is greater than or equal to the specified first threshold.

As a result of the identification at operation 1703, if the amount of change in pressure is less than the first threshold, the processor may maintain at operation 1703. On the other hand, as a result of the identification at operation 1703, if the amount of change in pressure is greater than or equal to the first threshold, the processor may wake up (or activate) a biometric sensor module (e.g., the biometric sensor module 220) at operation 1705. The processor may transmit, to the biometric sensor module, a first notification signal for waking up the biometric sensor module that is in an inactive state. In response to reception of the first notification signal, the biometric sensor module may be activated to identify the states of a plurality of electrodes (e.g., the first electrode 221, the second electrode 222, and the third electrode 223).

The processor may identify whether or not an interrupt signal is received from the biometric sensor module at operation 1707. If the first electrode, the second electrode, and the third electrode included in the biometric sensor module are electrically connected for a specified first time (e.g., 1 second) or more, the interrupt signal may be transmitted to the processor by the biometric sensor module.

As a result of the identification at operation 1707, if the interrupt signal (or a second notification signal) is not received, the processor may return to Operation 1703. On the other hand, if the interrupt signal is received as a result of the identification at operation 1707, the processor may determine that the electronic device is in a first context at operation 1709. The processor may determine that the electronic device in in a context in which the electronic device is underwater.

Operations 1711 to 1723 in FIG. 17 are the same as or similar to the operations 1611 to 1623 in FIG. 16, so a detailed description thereof will be omitted.

According to an embodiment, a method for recognizing a context of an electronic device (e.g., the electronic device 101, 201, 601) may include identifying whether an amount of change in the pressure detected through an atmospheric pressure sensor (e.g., the atmospheric pressure sensor 230) is greater than or equal to a specified first threshold, in response to the amount of change in the pressure being greater than or equal to the first threshold, waking up a biometric sensor module (e.g., the biometric sensor module 220) including a plurality of electrodes (e.g., the plurality of electrodes 221, 222, 223) in which some of the plurality of electrodes are disposed to come into contact with a body part of a user when the electronic device is worn, and others thereof are disposed to not come into contact with a body part of the user when the electronic device is worn, identifying whether an interrupt signal, indicating that a state in which the plurality of electrodes are electrically connected is maintained for a specified first time or more, is received from the biometric sensor module, and determining that the electronic device is in a specified first context in response to reception of the interrupt signal.

The method may further include identifying whether a change into another state in which the some electrodes are electrically connected is received from the biometric sensor module after the first context is determined, in response to the change into the another state being received, identifying whether the amount of change in the pressure detected through the atmospheric pressure sensor is greater than or equal to the first threshold, determining that the electronic device is in a specified second context in response to the amount of change in the pressure detected after the change into the another state is received being less than the first threshold and the state and the another state being repeated a specified number of times or more, and determining that the electronic device is in a specified third context in response to the amount of change in the pressure detected after the change into the another state is received being greater than or equal to the first threshold.

The method may further include, in response to a pressure greater than or equal to a specified second threshold being maintained for a specified third time or more, determining that the electronic device is in a specified fourth context, and in response to the state being maintained for a specified fourth time or more, determining that the electronic device is in a specified fifth context.

The method may further include executing a specified function or driving a specified mode, based on each context.

The electronic device may use a biometric sensor as a sensor for recognizing the external context, thereby preventing misrecognition (or misperception) of the external context and improving accuracy thereof. In addition, the electronic device does not require provision of a separate sensor for accurately recognizing the external context, thereby reducing the unit cost thereof. In addition, the electronic device may enable (or activate) the biometric sensor when entry into the water is sensed through the atmospheric pressure sensor, thereby preventing current consumption. In addition, the electronic device is able to recognize various external contexts through the biometric sensor and provide information related to the external contexts (e.g., underwater, swimming, loss, and the state of the user's clothing).

The electronic device may be one of various types of electronic devices. The electronic devices may include, for example, a portable communication device (e.g., a smartphone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used in connection with various embodiments of the disclosure, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138, the memory 320, 620) that is readable by a machine (e.g., the electronic device 101, 201, 601). For example, a processor (e.g., the processor 120, 310, 610) of the machine (e.g., the electronic device 101, 201, 601) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

A method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been shown and described with reference to certain embodiments thereof, it will be understood by those skilled in the art that various changes in form and details may be made therein without departing from the scope of the disclosure. Therefore, the scope of the disclosure should not be defined as being limited to the embodiments, but should be defined by the appended claims and equivalents thereof.

What is claimed is:
1. An electronic device comprising:
an atmospheric pressure sensor configured to measure pressure;
a biometric sensor module configured to measure biometric information on a user;
a processor operatively connected to the atmospheric pressure sensor and the biometric sensor module; and
a memory operatively connected to the processor,
wherein the biometric sensor module comprises a plurality of electrodes configured to detect current flowing through a body of the user,
wherein some of the plurality of electrodes are disposed to come into contact with a body part of the user when the electronic device is worn, and others of the plurality of electrodes are disposed to not come into contact with a body part of the user when the electronic device is worn,
wherein the biometric sensor module is configured to:
identify whether a change from a first state, in which the some of the plurality of electrodes are electrically connected through the body part and the others of the plurality of electrodes are electrically disconnected in air, into a second state, in which all of the plurality of electrodes are electrically connected by entering the electronic device in water, is detected,
identify whether the second state is maintained for a specified first time or more in response to the change into the second state being detected, and
transmit an interrupt signal to the processor in response to the second state being maintained for the specified first time or more, and
wherein the memory stores instructions that when executed, cause the processor to:
identify an amount of increased change in the pressure detected through the atmospheric pressure sensor in response to reception of the interrupt signal, and
determine that the electronic device is in a specified first context in response to the amount of increased change in the pressure being greater than or equal to a specified first threshold.

2. The electronic device of claim 1, wherein the memory stores instructions that, when executed, further cause the processor to:
- identify whether a change from the second state into the first state is received from the biometric sensor module after the first context is determined;
- in response to the change into the first state being received, identify whether an amount of decreased change in the pressure detected through the atmospheric pressure sensor is greater than or equal to the first threshold; and
- determine that the electronic device is in a specified second context in response to the amount of decreased change in the detected pressure being less than the first threshold and the first state and the second state being repeated a specified number of times or more.

3. The electronic device of claim 2, wherein the memory stores instructions that, when executed, further cause the processor to determine that the electronic device is in a specified third context in response to the amount of decreased change in the detected pressure being greater than or equal to the first threshold.

4. The electronic device of claim 1, wherein the memory stores instructions that, when executed, further cause the processor to:
- identify whether a pressure greater than or equal to a specified second threshold is maintained for a specified third time or more; and
- in response to the pressure greater than or equal to the specified second threshold being maintained for the specified third time or more, determine that the electronic device is in a specified fourth context.

5. The electronic device of claim 1, wherein the memory stores instructions that, when executed, further cause the processor to:
- identify whether the second state is maintained for a specified fourth time or more; and
- in response to the second state being maintained for the fourth time or more, determine that the electronic device is in a specified fifth context.

6. The electronic device of claim 1, wherein the biometric sensor module is configured to:
- identify whether a change from a third state, in which the plurality of electrodes are not electrically connected to each other, into the second state is detected, and
- in response to the change from the third state into the second state being detected, transmit the interrupt signal to the processor.

7. The electronic device of claim 1, wherein the memory stores instructions that, when executed, further cause the processor to execute a specified function or drive a specified mode, based on each context.

8. The electronic device of claim 1, wherein the plurality of electrodes comprises:
- a first electrode disposed to come into contact with a body part of the user when the electronic device is worn;
- a second electrode disposed to come into contact with a body part of the user when the electronic device is worn, and spaced apart from the first electrode; and
- at least one third electrode disposed to not come into contact with a body part of the user when the electronic device is worn,
- wherein the first electrode and the second electrode are disposed on the rear surface of the electronic device, and
- wherein the at least one third electrode is disposed on a side surface or an upper surface of the electronic device.

9. The electronic device of claim 1, wherein the biometric sensor module comprises:
- a detection module configured to detect an electrical connection state between the plurality of electrodes;
- a state information storage area configured to store information corresponding to the detected state; and
- a biometric information processing module configured to process the biometric information detected using at least some of the plurality of electrodes.

10. The electronic device of claim 9, wherein the biometric information processing module is activated while the biometric information is measured, and is deactivated while context recognition is executed.

11. An electronic device comprising:
- an atmospheric pressure sensor configured to measure pressure;
- a biometric sensor module configured to measure biometric information on a user;
- a processor operatively connected to the atmospheric pressure sensor and the biometric sensor module; and
- a memory operatively connected to the processor,
- wherein the biometric sensor module comprises a plurality of electrodes configured to detect current flowing through a body of the user,
- wherein some of the plurality of electrodes are disposed to come into contact with a body part of the user when the electronic device is worn, and others of the plurality of electrodes are disposed to not come into contact with a body part of the user when the electronic device is worn,
- wherein the biometric sensor module is configured to be activated in response to a wake-up signal being received from the processor, identify whether a state in which the plurality of electrodes are electrically connected by entering the electronic device in water is maintained for a specified first time or more, and transmit an interrupt signal to the processor in response to the state being maintained for the specified first time or more, and
- wherein the memory stores instructions that, when executed, cause the processor to transmit the wake-up signal to the biometric sensor module in response to an amount of increased change in the pressure measured through the atmospheric pressure sensor being greater than or equal to a specified first threshold, and determine that the electronic device is in a specified first context in response to reception of the interrupt signal from the biometric sensor module.

12. The electronic device of claim 11, wherein the memory stores instructions that, when executed, further cause the processor to:
- identify whether a change into another state in which a first electrode and a second electrode are electrically connected is received from the biometric sensor module after the first context is determined;
- in response to the change into the another state being received, identify whether an amount of change in the decreased pressure detected through the atmospheric pressure sensor is greater than or equal to the first threshold; and
- determine that the electronic device is in a specified second context, in response to the amount of change in the decreased pressure detected after the change into the another state is received being less than the first threshold and the state and the another state being repeated a specified number of times or more.

13. The electronic device of claim 12, wherein the memory stores instructions that, when executed, further cause the processor to determine that the electronic device is in a specified third context in response to the amount of decreased change in the detected pressure being greater than or equal to the first threshold after the change into the another state is received.

14. The electronic device of claim 11, wherein the memory stores instructions that, when executed, further cause the processor to:
identify whether a pressure greater than or equal to a specified second threshold is maintained for a specified third time or more; and
in response to the pressure greater than or equal to the specified second threshold being maintained for the specified third time or more, determine that the electronic device is in a specified fourth context.

15. The electronic device of claim 11, wherein the memory stores instructions that, when executed, further cause the processor to:
identify whether the state is maintained for a specified fourth time or more; and
in response to the state being maintained for the fourth time or more, determine that the electronic device is in a specified fifth context.

16. The electronic device of claim 11, wherein the memory stores instructions that, when executed, further cause the processor to execute a specified function or drive a specified mode, based on each context.

17. A method for recognizing a context of an electronic device, the method comprising:
identifying whether an amount of change in a pressure detected through an atmospheric pressure sensor is greater than or equal to a specified first threshold;
in response to an amount of increased change in the pressure being greater than or equal to the first threshold, waking up a biometric sensor module comprising a plurality of electrodes in which some of the plurality of electrodes are disposed to come into contact with a body part of a user when the electronic device is worn, and others thereof are disposed to not come into contact with a body part of the user when the electronic device is worn;
identifying whether an interrupt signal, indicating that a state in which the plurality of electrodes are electrically connected by entering the electronic device in water is maintained for a specified first time or more, is received from the biometric sensor module; and
determining that the electronic device is in a specified first context in response to reception of the interrupt signal.

18. The method of claim 17, further comprising:
identifying whether a change into another state in which the some of the plurality of electrodes are electrically connected is received from the biometric sensor module after the first context is determined;
in response to the change into the another state being received, identifying whether the amount of decreased change in the pressure detected through the atmospheric pressure sensor is greater than or equal to the first threshold;
determining that the electronic device is in a specified second context in response to the amount of decreased change in the pressure detected after the change into the another state is received being less than the first threshold and the state and the another state being repeated a specified number of times or more; and
determining that the electronic device is in a specified third context in response to the amount of decreased change in the pressure detected after the change into the another state is received being greater than or equal to the first threshold.

19. The method of claim 17, further comprising:
in response to a pressure greater than or equal to a specified second threshold being maintained for a specified third time or more, determining that the electronic device is in a specified fourth context; and
in response to the state being maintained for a specified fourth time or more, determining that the electronic device is in a specified fifth context.

20. The method of claim 17, further comprising executing a specified function or driving a specified mode, based on each context.

* * * * *